United States Patent [19]
Horn et al.

[11] Patent Number: 5,596,131
[45] Date of Patent: Jan. 21, 1997

[54] REGENERATION OF GRAMINACEOUS PLANTS OF THE SUBFAMILY POOIDEAE FROM PROTOPLASTS

[75] Inventors: Michael E. Horn, Woodland, Calif.; Christian T. Harms; Raymond D. Shillito, both of Chapel Hill, N.C.

[73] Assignee: Ciba-Geigy Corporation, Tarrytown, N.Y.

[21] Appl. No.: 486,059

[22] Filed: Jun. 7, 1995

Related U.S. Application Data

[63] Continuation of Ser. No. 271,226, Jul. 6, 1994, abandoned, which is a continuation of Ser. No. 56,965, May 3, 1993, abandoned, which is a continuation of Ser. No. 611,371, Nov. 13, 1990, abandoned, which is a continuation of Ser. No. 165,665, Mar. 8, 1988, abandoned.

[51] Int. Cl.⁶ .............................. A01H 4/00; C12N 5/14
[52] U.S. Cl. .................. 800/205; 800/DIG. 55; 435/240.47; 435/240.49; 435/240.5
[58] Field of Search .................. 435/240.4–240.45, 435/240.46, 240.47, 240.48, 240.49, 240.5; 800/200, 205, DIG. 55

[56] References Cited

U.S. PATENT DOCUMENTS

| | | | |
|---|---|---|---|
| 4,672,035 | 6/1987 | Davidonis et al. | 435/240.4 |
| 5,187,073 | 2/1993 | Goldman et al. | 435/172.3 |

FOREIGN PATENT DOCUMENTS

| | | | |
|---|---|---|---|
| 0176162 | 4/1986 | European Pat. Off. | |
| 0257472 | 3/1988 | European Pat. Off. | 800/205 |

OTHER PUBLICATIONS

Gray et al., Biological Abstracts, vol. 79 (1985) Abstract #18364.
Kyozuka et al (1987) Mol. Gen. Genet. 206: 408–413.
Lorz et al (1985) Mol. Gen. Genet. 199: 178–182.
Fromm et al (1986) Nature 319: 791–793.
Papenfuss et al (1987) Crop Science 27: 588–593.
Hanning et al (1986) J. Plant Physiol. 123: 23–29.
Dalton et al. (1988) Plant Cell, Tissue and Organ Culture 12: 137–140.
Vasil, et al. (1980) Theor. Appl. Genet. 56: 97–99.
Potrykus et al., Mol. Gen. Genet., 199:183–188 (1985).
Maddock, Biological Abstracts, vol. 83 (1987), Abstract #122226.
Dalton et al., Biological Abstracts, vol. 86 (1988), Abstract #33950.
Horn et al., Biological Abstracts, vol. 86 (1988), Abstract #43934.
Horn et al., Chemical Abstracts, vol. 11 (1989), Abstract #89869a.
Kao et al., Colloq. Int. C.N.R.S., 212:207–213 (1973).
Dongfeng et al, Scientia Sinica, 30:698–703 (1987).
E. C. Cocking et al, Science 236: 1259–1262 (1987).
M. G. K. Jones in: "Cereal tissue and cell culture" S. W. J. Bright and M. G. K. Jones, editors), Nyhoff/ Dr. W. Junk, Dordrecht (1985) pp. 204–230.
R. Abdullah et al., Bio/Technology 4: 1087–1090 (1986).
Y. Yamada et al., Plant Cell Reports 5: 85–88 (1986).
C. A. Rhodes et al., Bio/Technology 6: 56–60 (1988).
G. E. Hanning and B. V. Conger, Theor. Appli. Genet. 63: 155–159 (1982).
B. S. Ahloowalia in: "Handbook of Plant cell Culture" (P. V. Ammirato et al., editors), Macmillan, New York 1984, pp. 91–125.
K. J. Webb, Plant Cell, Tissue and Organ Culture 12: 127–131 (1988).
M. R. Davey et al. Plant Cell, Tissue and Organ Culture 12: 115–125 (1988).
L. A. Withers in: "Plant tissue culture and its agricultural application" (L. A. Withers and P. G. Alderson, editors), Butterworth, London, 1986, pp. 261–276.
L. A. Withers in: "Cell culture and somatic cell genetics of plants", vol. 2 (I. K. Vasil, editor) Academic Press, New York, 1985, pp. 253–316.
L. A. Withers in: "Cell culture and somatic cell genetics of plants", vol. 1 (I. K. Vasil, editor), Academic Press, New York, 1984, pp. 608–620.
T. H. H. Chen et al., Plant Cell, Tissue and Organ Culture 4: 101–109 (1985).
B. J. Finkle and J. M. Ulrich in: "Plant cold hardiness and freezing stress" (P. H. Li and A. Sakai, editors) Academic Press, New York, 1978, pp. 373–388.
L. C. Jian et al. in: "Plant cold hardiness" (P. H. Li, editor), Alan R. Liss, Inc., New York, 1987, pp. 323–337.
G. Hahne and H. Lörz, Plant Breeding 99: 330–332 (1987).
S. L. Reece and S. E. Maddock, In Vitro 24: 33A, abstract 86 (1988).

Primary Examiner—Che S. Chereskin
Attorney, Agent, or Firm—James S. Elmer

[57] ABSTRACT

The present invention provides cell cultures derived from graminaceous plants which cultures are capable of being regenerated into plants, including fertile plants. Methods of accomplishing this regeneration are also provided. In addition, a novel procedure for the cryopreservation of embryogenic cell cultures is described.

13 Claims, 6 Drawing Sheets

REGENERATION OF GRAMINACEOUS PLANTS OF THE SUBFAMILY POOIDEAE FROM PROTOPLASTS

This application is a continuation of 08/271,226 filed Jul. 6, 1994, now abandoned, which is a continuation of 08/056,965 filed May 3, 1993, now abandoned, which is a continuation of 07/611,371 filed Nov. 13, 1990, now abandoned, which is a continuation of 07/165,665 filed Mar. 8, 1988, now abandoned.

FIELD OF THE INVENTION

The present invention relates to graminaceous plants of the subfamily of the Pooideae that are regenerated from protoplasts or from protoplasts with regenerated cell walls (plant cells) or from protoplast-derived calli and to generally applicable methods for regeneration of these plants. It also relates to the embryogenic cell cultures (suspension cultures or callus cultures) and calli that constitute the source for protoplasts which can be regenerated into plants. It further relates to the methods of producing the embryogenic cell cultures mentioned above, to the cryo-preservation of said embryogenic cell cultures and of the embryogenic calli, and to transgenic Pooideae plants regenerated from genetically modified protoplasts.

BACKGROUND OF THE INVENTION

Most of the plant species upon which Mankind is dependent for the bulk of its diet belong to that group of plants known collectively as the Gramineae. The Gramineae (Poaceae) are, from a commercial point of view, the most important family within the class of monocotyledonous plants. The Gramineae embrace, for example, the following subfamilies and genera:

| Subfamily | Genus within the subfamily |
| --- | --- |
| Bambusoideae | Bamboo |
| Andropogonoideae | Saccharum [sugarcane] |
| | Sorghum |
| | Zea [corn] |
| Arundineae | Phragmites |
| Oryzoideae | Oryza [rice] |
| Panicoideae | Panicum (*) |
| | Pennisetum (*) |
| | Setaria (*) |
| Pooideae (Festuciadeae) | Poa (**) |
| | Festuca (**) |
| | Lolium (**) |
| | Bromus (**) |
| | Trisetum (**) |
| | Agrostis (**) |
| | Phleum (**) |
| | Dactylis (**) |
| | Alopecurus (**) |
| | Avena [oats] (ˆ) |
| | Triticum [wheat] (ˆ) |
| | Secale [rye] (ˆ) |
| | Hordeum [barley] (ˆ) |
| | Sorghum [tz,1/32 |

(*) (millets)
(**) (grasses)
(ˆ) (small grain cereals)

Among the subfamilies of the Gramineae the family Pooideae is a group of economically highly important plants that includes, for example, the two closely related subgroups consisting of the grasses and the small grain cereals.

Interestingly these Pooideae plants have also been the most difficult to manipulate scientifically. Until now, no generally applicable method is known for the regeneration of Pooideae plants, or fertile Pooideae plants, or for Pooideae plants containing stably incorporated exogenous DNA from protoplasts, although plant regeneration from cultured protoplasts is essential for the application of somatic hybridization and direct gene transfer. The present state of the art in gene transfer into cereals has recently been reviewed by Cocking, E. C., and Davey, M. R. [Science, 236 (1987) 1259–1262].

Sources for cereal cultures, protoplasts, the isolation of cereal protoplasts, and their properties are reported, for example, in the following book: ["Cereal Tissue and Cell Culture" Bright, S. W. J. and Jones, M. G. K., (eds) (1985) Nijhoff, M./Junk, W. Dr., Dordrecht].

Stable transformation has been already achieved in the Gramineae by chemically and electrically stimulated uptake of DNA into protoplasts ("direct gene transfer") [Potrykus, I., et al., Mol. Gen. Gent., 199 (1985) 183–188; Loerz, H., et al., Mol. Gen. Gent., 199 (1985) 178–182; Fromm, M. E., et al., Nature, 319 (1986) 791–793], but plant regeneration was not possible from the lines used in these studies.

So far, graminaceous plants have only been successfully regenerated from protoplasts other than of the subfamily Pooideae: For example, Abdullah, R., et al. [Bio/Technology, 4 (1986) 1087–1090] report the efficient plant regeneration from rice (subfamily: Oryzoideae) protoplasts through somatic embryogenesis. Yamada, Y., et al. [Plant Cell Reports, 5 (1986) 85–88] also describe rice plant regeneration from protoplast-derived calli. Also Rhodes, C., et al. [Biotechnology, 6 (1988) 56–60] describe the regeneration of non-fertile plants of maize. Cocking, E. C., and Davey, M. R. [supra] discuss the present state of the art in gene transfer in cereals.

The regeneration of graminaceous plants of the subfamily Pooideaefrom tissue cultures is known: Hanning, G. E., et al. [Theor. Appl. Genet., 63 (1982) 155–159] describe embryo and plantlet formation from leaf segment-derived callus of *Dactylis glomerata* L.

Some further examples of regeneration of Pooideae plants from cultured cells are reported in the following articles:

*Lolium rigidum:* Skene, K. G. M., et al., Zeitschr. Pflanzenzüchtung, 90 (1983) 130–135.

*Lolium perenne, Lolium multiflorum:* Ahloowalia, B. S., Crop Science, 15 (1975) 449–452.

*Lolium multiflorum, Festuca arundinacea:* Kasperbauer, M. J., et al., Crop Science, 19 (1979) 457–460.

*Alopecurus arundinaceus, Agropyron crystatum, Stipa viridula, Bromus inermis, Agropyron smithii:* Lo, P. F., et al., Crop Science, 20 (1980) 363–367.

*Agrostis palustris:* Krans, J. V., et al., Crop Science, 22 (1982) 1193–1197.

The state of tissue culture in forage grasses has also been reviewed by Ahloowalia, B. S. [Handbook of Plant Cell Culture, Ammirato et al. (eds), Macmillan, New York (1984) 91–125].

However, these Pooideae plants were not regenerated in these cases from the type of starting material described in the present application but from other types of cell cultures. It has not been demonstrated in the above examples that regeneration was de-novo by way of somatic embryogenesis. The above quoted references did not comprise the isolation and culture of protoplasts or the regeneration of plants from protoplasts.

Although there has been great interest in genetic transformation and regeneration of graminaceous plants of the subfamily Pooideae, there has been no description to date of a successful in-vitro method which can lead to regenerated, optionally transformed, protoplast-derived, plants or fertile plants (Cocking E. C. and Davey, M. R. [supra]).

Until now all investigations and every effort made in this direction failed, in so far as they resulted in embryos or at most in non-viable plantlets that died in an early stage and therefore could not be successfully transferred to soil [Ahloowalia, B. S. [Handbook of Plant Cell Culture, Ammirato et al. (eds), Macmillan, New York (1984) 91–125].

No description of a procedure for producing Pooideae protoplasts capable of undergoing differentiation to plants and whole fertile plants, much less of the regeneration of Pooideae plants from protoplasts or protoplast-derived calli, has appeared.

SUMMARY OF THE INVENTION

These and other objectives have been achieved in accordance with the present invention which provides a method for producing protoplasts that can form cell and callus colonies. The protoplasts can, if desired, be transformed, and the resultant calli are capable of being regenerated into Pooideae plants. The process for producing protoplasts capable of dividing and forming callus, which then can be regenerated into plants, requires as a starting material a novel embryogenic cell cultures (suspension cultures or callus cultures) or embryos. Such embryogenic cell cultures, embryos and methods for producing and identifying them will be described, and are considered part of the invention. Embryogenic callus from which the suspensions are derived can also be used as a starting material for protoplasts. Such callus and suspensions, embryos and methods for producing and identifying them will be described, and are also considered part of the present invention.

These embryogenic cultures are the source of protoplasts capable of being transformed with exogenous DNA, and of dividing and forming callus, which then can be regenerated into plants, including whole, fertile plants that can grow in soil.

One could not predict from the prior art at the time this invention was made, that graminaceous plants, particularly fertile graminaceous plants, of the subfamily Pooideae could be regenerated from protoplasts, from protoplast-derived cells or protoplast-derived calli. Even less predictable was that Pooideae protoplasts containing stably incorporated exogenous DNA could also be regenerated into transgenic plants, particularly into fertile transgenic plants.

OBJECTS OF THE INVENTION

This invention is directed to embryogenic cell cultures (suspension cultures or callus cultures) derived from graminaceous plants of the subfamily Pooideae from which protoplasts can be isolated, wherein the protoplasts regenerate cell walls, divide and form callus capable of being regenerated into plants, including fertile plants.

This invention also relates to Pooideae protoplasts and the resulting plant cells (after regeneration of the cell walls) that can be regenerated into plants which are preferably fertile, preferably to such protoplasts derived from cell cultures or from embryogenic cell suspensions.

This invention also relates to plant cells, calli, embryogenic suspensions, embryos, plantlets and plants derived from said protoplasts.

Furthermore, this invention relates to the regenerated Pooideaeplants and propagules thereof, especially to those derived from protoplasts or plant cells containing stably incorporated exogenous DNA, preferably exogenous DNA expressible in plants. Propagules include any material that can be sexually or asexually propagated or propagated in-vivo or in-vitro. Among this material protoplasts, cells, calli, tissues or seeds obtained from transgenic Pooideae plants are preferred. The progeny of said Pooideae plants, including mutants and variants thereof, including those of plants obtained from somatic cell fusion, genetic modification, or mutant selection, are further objectives of this invention.

This invention also relates to a method of producing Pooideaeprotoplasts and Pooideae plant cells that can be regenerated into plants, particularly into fertile plants, moreover, to a method of producing Pooideae calli derived from said protoplasts or plant cells and being capable of regeneration into plants, preferably into fertile plants. In addition, it relates to a method of regenerating Pooideae plants, from these calli. These methods are described in detail hereinafter.

These and further objects will become available from the following detailed description.

Figure 1:
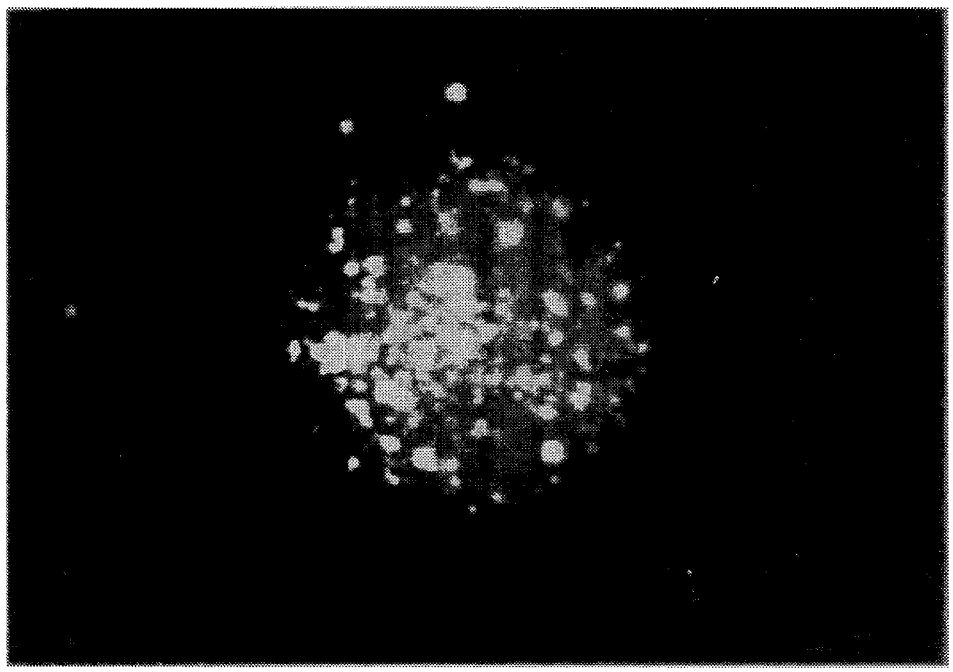
FIG. 1 shows protoplast-derived colonies of *Dactylis glomerata L.* growing in an agarose bead suspended in liquid medium.
Figure 2:
FIG. 2 shows a plantlet arising from protoplast-derived callus *Dactylis glomerata L.* growing on SH-0 medium.
Figure 3:
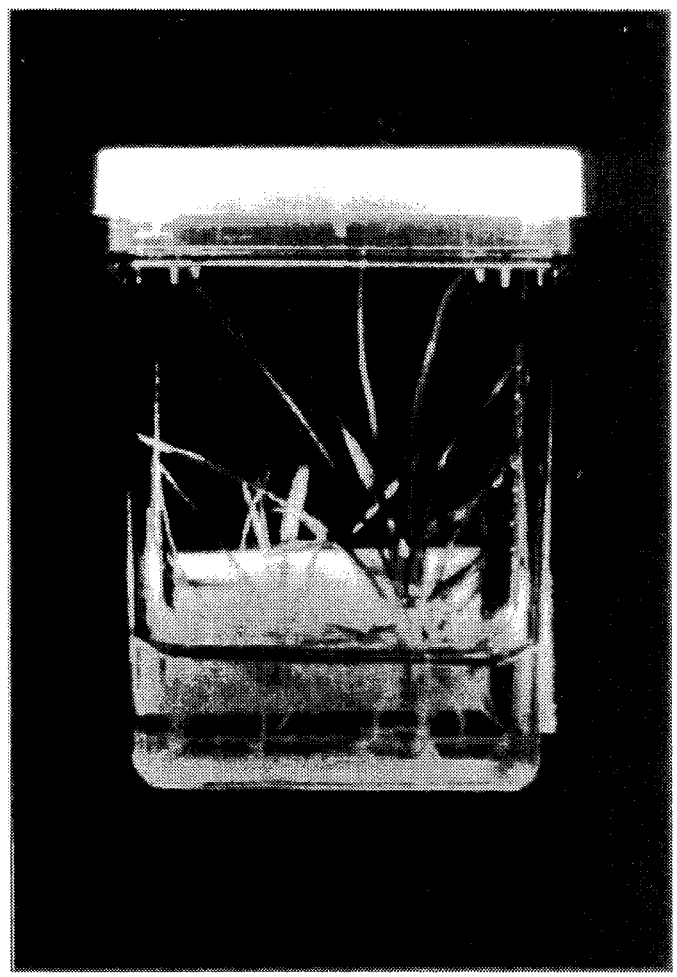
FIG. 3 shows rooted plantlet from protoplast-derived callus *Dactylis glomerata L.* growing on SH-0 medium in a container.
Figure 4:
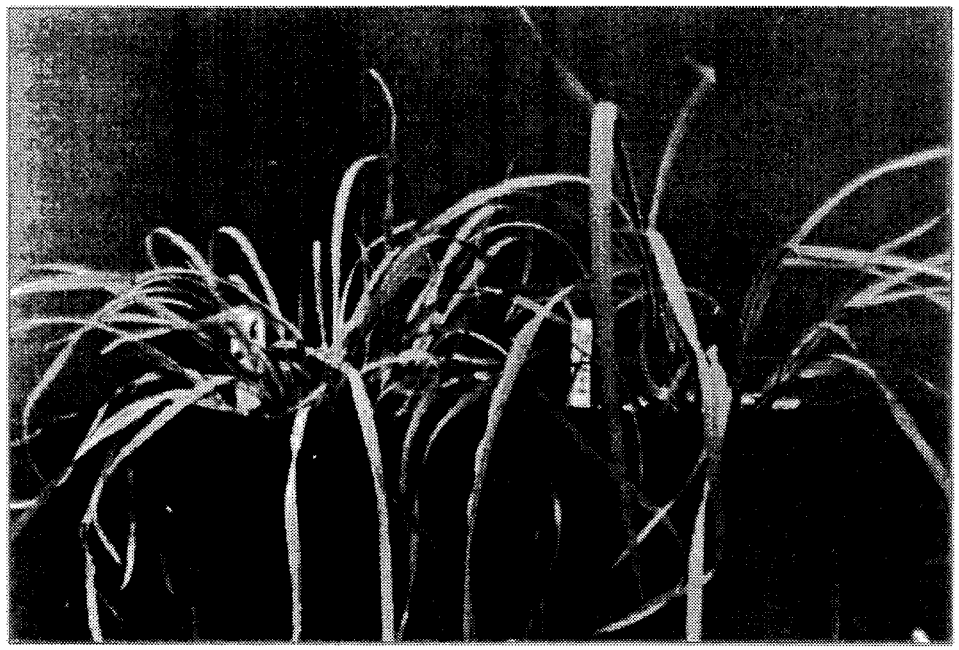
FIG. 4 shows a plant of *Dactylis glomerata L.* regenerated from protoplasts (on left) together with a wild type *Dactylis glomerata L.* plant (on right).
Figure 5:
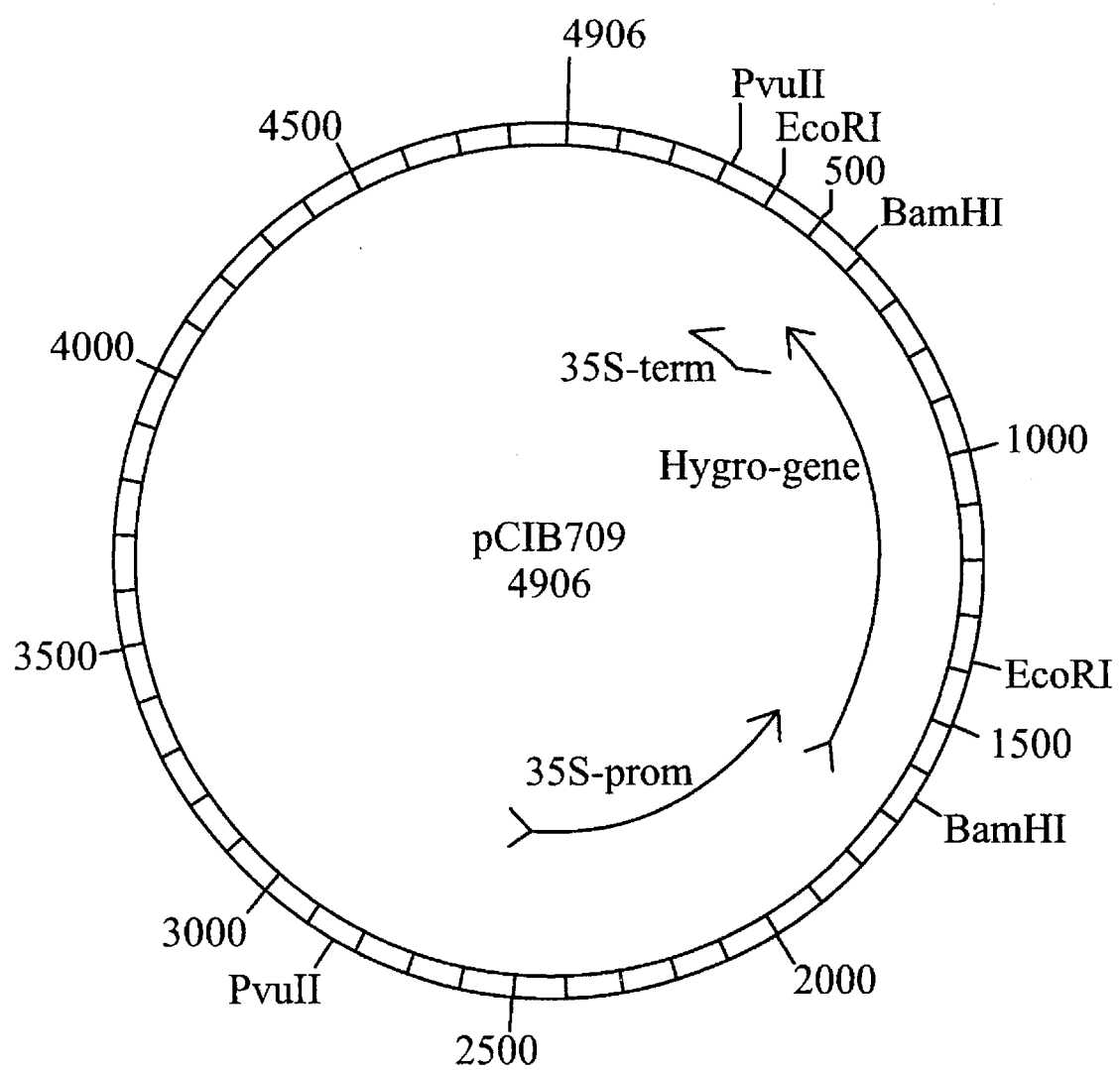
FIG. 5 shows the plasmid pCIB709 used for transformation of *Dactylis glomerata L.* protoplasts to confer resistance to hygromycin Plasmid pCIB709 has been deposited in accordance with requirements of the Budapest Treaty in the ATCC and has accession number ATCC 40428. The date of this deposit is Feb. 12, 1988.
Legend:
- 35S prom: 35S promotor region.
- Hygro-gene: Hygromycin phosphotransferase (APH type IV) structural gene.
- 35S term: region of CaMV containing the 3' polyadenylation site of the 35S transcript of CaMV.
Figure 6:
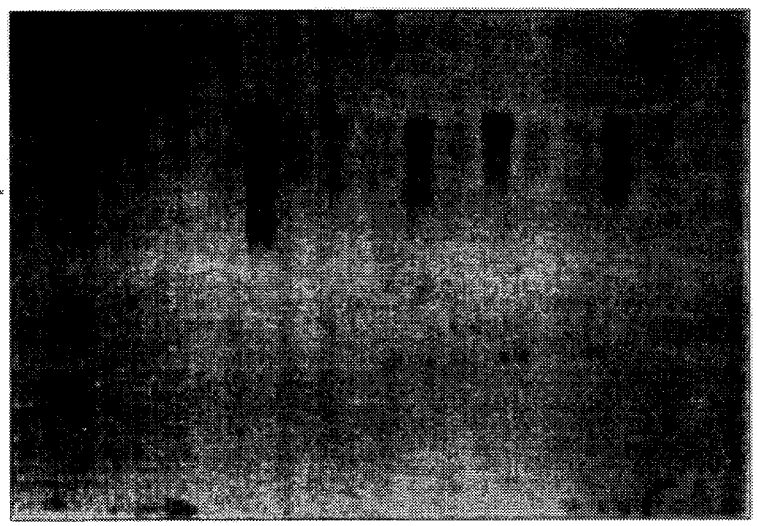
FIG. 6 shows the Southern analysis of different *Dactylis glomerata L.* calli recovered after transformation of protoplasts pCIB709, probed with the XbaI-SstI fragment of pCIB709.

| | |
|---|---|
| Lanes 1, 2: | 10 and 2ng pCIB709 cut with restriction endonuclease BamH1. |
| Lanes 4–8: | DNA from *Dactylis glomerata L. callus* cultures recovered after transformation of with pCIB709, cut with BamH1. |
| Lanes 9, 17: | DNA from control untransformed *Dactylis glomerata L. callus* derived from protoplasts, with BamH1. |
| Lanes 10–13: | DNA from *Dactylis callus* cultures recovered after transformation of protoplasts with pCIB709, cut with BamH1. |
| Lane 14: | DNA from *Dactylis glomerata L. callus* cultures recovered after transformation of protoplasts with pCIB709, cut with BamH1. |
| Lanes 15, 16: | DNA from *Dactylis glomerata L. callus* cultures recovered after transformation of protoplasts with pCIB709, cut with BamH1. |
| Lanes 4: | is empty. |

The DNA in lanes 6, 10, 12, and 15 shows the presence of foreign DNA integrated into the genome of the *Dactylis glomerata L.* cells as evidenced by the darkening of the film. The 1063bp fragment expected from BamHI digestion of the integrated hygromycin gene of pCIB709 (nucleotides 583–1646 of pCIB709) is indicated by the arrow.

DETAILED DESCRIPTION OF THE INVENTION

Definitions

In order to provide a clear and consistent understanding of the specification and the claims, including the scope given to such terms, the following definitions are provided:

Plant Cell: The structural and physiological unit of plants, consisting of a protoplast and the cell wall.

Plant Tissue: A group of plant cells organized into a structural and functional unit.

Plant Organ: A distinct and visibly differentiated part of a plant such as root, stem, leaf, flower bud, or embryo. A plant organ may consist of different types of plant cells or plant tissues.

Protoplast: Isolated plant cell without a cell wall.

Cell Culture: Proliferating mass of cells in an undifferentiated or partially differentiated state.

Embryo: A minute early developmental stage of a plant, either derived from a zygote (sexual embryo) or from an embryogenic somatic cell (somatic embryo), with stages of recognizable morphology, structure and cellular organization comprising cellular to globular to cotyledonary stages. [Corn embryo development is, for example, described in Randolph, L. F., J. Agric. Research, 53 (1936) 881–916; grass embryo development is, for example, described in Brown, W. V., Phytomorphology, 10 (1960) 215–223.]

Cell cluster: A group of interconnected cells attached to each other; usually derived from one or a few ancestral cells or protoplasts by cell division.

Plantlet: A multicellular structure made up of a shoot and root in the form of a small plant.

Dicamba: 3,6-dichloro-2-methoxy benzoic acid.

MES: 2-[N-morpholino]ethane sulfonic acid.

2,4-D: 2,4-dichlorophenoxyacetic acid.

Picloram: 4-amino-3,6,6-trichloropicolinic acid.

Tris-HCl: alpha,alpha,alpha-tris(hydroxymethyl)methylamine hydrochloride.

EDTA: 1-ethylendiamine N,N,N',N'-tetraacetic acid

PEG: polyethylene glycol

Agarose: Preparation and purification of agarose are described, for example by Guiseley and Renn, ["The Agarose Monograph", Marine Colloids Division FMC Corp.(1975)]. Agarose is one of the constituents of agar. Commercially available agar normally consists of a mixture of neutral agarose and ionic agaropectin with a large number of side groups. Commercial agarose is normally obtained from agar by conventional methods. Usually a certain number of side chains remains intact and determines the physicochemical properties of the agarose, such as gel formation and melting temperature. Low-melting agarose, especially SeaPlaque® agarose, is a preferred solidifying agent within the process described hereinafter.

SH-0 medium: Medium of Schenk, R. U. and Hildebrandt, A. C., Can. J. Bot., 50 (1972) 199–204; without hormones. (SH medium can be liquid or solidified with 0.8% (w/v) agar or with 0.5% (w/v) GelRite®). The medium is normally sterilized by heat or sterilized by autoclaving at 121° C. and 15 lb/in$^2$ pressure for about 15 to 20 minutes as known in the art.

GelRite®: GelRite Gellan Gum, Scott Laboratories Inc., Fiskersville, R.I. 02823.

SH-30 medium: SH-0 medium containing 30 μm Dicamba.

SH-45 medium: SH-0 medium containing 45 μm Dicamba.

KM-8p medium: Medium 8p of Kao, K. N., et al., Planta, 126 (1975) 105–110. This medium may be liquid or solidified with agar, agarose or GelRite®, and may equally well be prepared and used without ascorbic acid, vitamin D, and vitamin A. The medium components except solidifying agent are normally sterilized by filtration through a 0.2 μm filter.

RY-2 medium: Medium of Yamada, Y., et al., Plant Cell Reports, 5 (1986) 85–88.

OMS medium: Medium of Murashige, T. and Skoog, F., Physiologia Plantatum, 15 (1962) 473–497. The medium can be solidified, for example, with 0.8% (w/v) agar or agarose or with 0.5% (w/v) GelRite®. For the purposes described in this paper, this medium can also be prepared such that it contains the vitamin composition of the B5 medium of Gamborg O. L. et al. [Exp. Cell Res., 50, 151–158, 1968].

Cellulase RS: Cellulase RS, Yakult Honsha Co. Ltd., 1.1.19 Higashi-Shinbashi, Minato-ku, Tokyo 105, Japan.

Pectolyase Y-23®: Seishin Pharmaceutical Co. Ltd., 4-13 Koami-cho, Nihonbashi, Tokyo, Japan.

Parafilm®: Parafilm® laboratory film—American Can Co. Greenwich, Conn., 06830, USA.

Nalgene® filter: Nalge Co., Division of Sybron Corp. Rochester, N.Y., 14602, USA.

BglII: Restriction enzyme BglII; New England Biolabs, 32 Tozer Road, Beverly, Mass., 01915, USA, or any other commercial supplier.

BamHI: Restriction enzyme BamHI; New England Biolabs, 32 Tozer Road, Beverly, Mass., 01915, USA, or any other commercial supplier.

Casein hydrolysate: Casein Hydrolysate—Enzymatic Hydrolysate from bovine milk, Type 1, Sigma Co. PO. Box 14508, St. Louis, Mo. 63178, USA.

Hygromycin B: Cytotoxin: Hygromycin B, purified; Cat No. 400050 Calbiochem Behring Diagnostica, La Jolla, Calif. 92037, USA, Lot No. 702296.

GeneScreen Plus®: Cat. No. NEF 976, NEN Research Products, 549 Albany St., Boston, Mass. 02118, USA.

TBE buffer: Tris-borate buffer—common buffer for electrophoresis, see Maniatis et al. "Molecular Cloning, a Laboratory Manual" Cold Spring Habor Laboratory (1982).

Spin column: Sephadex® G25 prepacked column, Cat.No. 100402, Boehringer Mannheim Biochemicals, Piscataway, N.J., USA.

SDS: Sodium dodecyl sulfate.

SSC: 1.54 mM NaCl, 0.154 mM Na citrate as described in Maniatis et al. supra.

CETAB: Hexadecyltrimethylammonium bromide.

IBI Random primer kit: 'Prime Time' random primer kit, International Biotechnologies Inc., PO. Box 1565, New Haven, Conn. 07606, USA. (Catalog No. 77800; lot No. F630-01)

It has now been found that graminaceous plants, including fertile graminaceous plants, of the subfamily Pooideae can be regenerated from a specific type of protoplasts and from cells or callus derived from these protoplasts.

This regeneration of plants, including fertile plants is also possible if the protoplasts contain exogenous DNA, preferably stably incorporated exogenous DNA capable of being expressed in plants.

Any graminaceous plant of the subfamily Pooideae may be used in the present invention. Preferred, however, are Pooideae plants belonging to the grasses, for example, each genus selected from the group consisting of Poa, Festuca, Lolium, Bromus, Trisetum, Agrostis, Phleum, Alopecurus and Dactylis. Most preferred is Dactylis. Also preferred are Pooideae plants belonging to the small grain cereals, for example, each genus selected from the group consisting of Avena (oats), Triticum (wheat), Secale (rye) and Hordeum (barley).

The specific type of Pooideae protoplasts that divide and form cell cultures capable of being regenerated into plants originate from cell cultures, preferably embryogenic cell cultures. The embryogenic cell cultures are preferably embryogenic suspensions or embryogenic callus cultures. The cell cultures may be derived from suitable parts of Pooideae plants. Suitable parts of plants include but are not limited to the basal parts of young inner leaves, immature sexual embryos, immature inflorescences, mature seeds or seedling tissues of Pooideae plants.

Step A: Preparation of Embryogenic Suspensions from Tissue

Embryogenic callus is initiated from a suitable part of a Pooideae plant, typically from the basal portion of young leaves, most preferably the younger, inner leaves of a Pooideae plant. This can be carried out as described for *Dactylis glomerata L.* by Hanning, G. E., et al. [Theor. Appln. Genet.,63 (1982) 155–159] but can also be used for all other Pooideae plants. This publication is incorporated herein by reference. The leaves are, for example, sliced in small sections or segments about 1 to 5 mm in length or diameter. Form and size of these pieces are not critical. These segments are plated on a suitable callus inducing and maintenance medium and cultured until callus and/or embryogenic structures develop. A suitable medium is, for example, SH medium [Schenk, R. U. and Hildebrandt, A. C., Can. J. Bot., 50 (1972) 199–204] containing 30 µM dicamba and 0.8% (w/v) agar or agarose as a gelling agent. Among other suitable media are those described in George E. F. et al. (eds), Exegetics Ltd., Edington, Westbury, Wiltshire, England (1987). Callus and/or embryogenic structures usually appear within 2 to 6 weeks after plating. Initiation and maintenance may be carried out in the light or preferably in the dark and at temperatures between 0° and 50° C., preferably 20° and 32° C., most preferably 25° and 28° C. Embryogenic callus may also be prepared by other methods known in the art, such as those to for Barley by Lührs R. and Lörz H. [Theor. Appl. Genet., 75, (1987) 16–25] and references contained therein. These methods can be used for other Pooideae and are incorporated by reference.

Embryogenic suspension cultures are initiated by putting fresh pieces of the embryogenic callus into a suitable liquid medium, for example, 0.5 g callus in 50 ml of a liquid medium as described by Gray, D. J., et al. [Plant Cell Tissue Organ Cult., 4 (1985) 123–133] containing 45 µM dicamba and 4 g/liter casein hydrolysate. Among other suitable media are those described in George E. F. et al. (eds), Exegetics Ltd., Edington, Westbury, Wiltshire, England (1987). The suspension cultures are grown at temperatures between 10° and 40° C., preferably 20° C. and 32° C., most preferably between 25° and 30° C. Succession of light and dark phases during the culturing period can be of advantage. The suspension is preferably grown under a 5 to 20, preferably 16 hours light period followed by a 5 to 20, preferably 8 hours, dark period. The light intensity is typically between 0.1 and 100 µE/m$^2$sec (E=Einstein; m=meter; sec=second), preferably between 30 and 80 µE/m$^2$sec. Shaking of the suspension during the culturing period is also advantageous. Shaking can be carried out, for example, on a gyratory shaker at about 100 to 150 rpm in Delong flasks sealed with a plastic film that is permeable to light and gases or any other suitable closure. After approximately three to five weeks the larger clumps are allowed to settle for about 30 seconds and the supernatant medium containing small cell clusters is removed and transferred to fresh medium to initiate new cultures.

This procedure can be repeated periodically, preferably every 3 to 4 weeks, using the most successful cultures as judged by smaller clump size and quality. After 4 to 20, usually 6 to 8, transfers the suspensions are essentially free of non-embryogenic cells and the majority of the embryogenic cell clusters are typically about 150 to 2000 µm in size.

In the procedure for obtaining embryogenic suspensions it is preferred that the suspensions consist predominantly of small pre-embryogenic masses. By subculturing only the upper part of the suspension after allowing the larger material to settle it is possible to enrich significantly the proportion of pre-embryogenic masses.

Thus, one objective of the present invention is the embryogenic cell culture, suspension culture or callus culture, derived from graminaceous plants of the subfamily Pooideae from which protoplasts can be isolated, wherein the protoplasts regenerate cell walls, divide and form callus capable of being regenerated into plants and fertile plants.

Embryogenic cell cultures (suspension cultures and callus cultures) derived from grasses, especially from those selected from the genera consisting of Poa, Festuca, Lolium, Bromus, Trisetum, Agrostis, Phleum, Alopecurus and Dactylis are preferred embodiments of the present invention. Mostly preferred are embryogenic suspensions of *Dactylis glomerata L.*.

Further preferred embodiments of the present invention consist of embryogenic cell cultures (suspension cultures and callus cultures) derived from small grain cereals, especially from those selected from the genera consisting of Avena, Triticum, Secale and Hordeum.

A further objective of the present invention is the embryogenic callus derived from graminaceous plants of the subfamily Pooideae from which protoplasts can be isolated, wherein the protoplasts regenerate cell walls, divide and form callus capable of being regenerated into plants and preferably into fertile plants.

Embryogenic callus derived from grasses, especially from those selected from the genera consisting of Poa, Festuca, Lolium, Bromus, Trisetum, Agrostis, Phleum, Alopecurus and Dactylis are preferred embodiments of the present invention. Mostly preferred is embryogenic callus of *Dactylis glomerata L.*.

Further preferred embodiments of the present invention consist of embryogenic callus derived from small grain cereals, especially from those selected from the genera consisting of Avena, Triticum, Secale and Hordeum.

Methods for the Cryopreservation of Cell Cultures (Suspension Cultures and Callus Cultures) of all Graminaceous Plants Some plant tissues can be cryopreserved by methods known in the art [Withers, L. A., in: Plant tissueculture and its agricultural application,; Withers, L. A., and Alderson, P.

G. (eds), University Press, Cambridge, England (1986) 261–276; and the references cited therein]. However, these methods are not generally applicable, especially not to the cryopreservation of embryogenic cell cultures (suspension cultures and callus cultures) of graminaceous plants.

It now has surprisingly been found that embryogenic cell cultures, including suspension cultures and callus cultures of all graminaceous plants can be preserved in a suspended state by freeze preservation (cryopreservation) at low temperatures.

This method for cryopreserving embryogenic cell cultures, including suspension cultures and callus cultures of graminaceous plants comprises:

(a) dispersing actively growing suspension culture cells or callus in a suitable liquid culture medium,
(b) cooling down this culture to ice temperature (about 0° to 5° C.),
(c) mixing at about the same temperature said pre-cooled culture with a suitable cryoprotecting aqueous solution,
(d) cooling the resultant mixture at a rate of about 0.01° to about 20° C. per minute, preferably about 0.1° to about 5° C. per minute, more preferably about 0.2° to about 2° C. per minute, most preferably 0.5° to 1° C. per minute, to a temperature of between about −20° and about −60° C., preferably between −35° and −50° C., most preferably about −38° and about −44° C.,
(e) shock-freezing the pre-cooled mixture in liquid nitrogen or liquid air, and
(f) storing the frozen mixture at a temperature below −100° C., preferably at the temperature of liquid nitrogen or liquid air.

This method for cryopreservation of embryogenic cell cultures (suspension cultures and callus cultures) is generally applicable for all Graminaceos plants. It is understood that in this context the term graminaceous plants includes but is not limited to the Bambusoideae (for example, Bamboo), the Andropogonideae (for example, Saccarum, Sorghum and Zea), the Arundineae (for example, Phragmites), the Oryzoideae (for example, Oryza), the Panicoideae (for example, Panicum, Pennisetum and Setaria) and the Pooideae (for example, grasses including Poa, Festuca, Lolium, Bromus, Trisetum, Agrostis, Phleum, Dactylis and Alopecurus, or small grain cereals including Avena, Triticum Secale and Hordeum).

A preferred target group within the graminaceous plants is the above characterized group of Pooideae plants consisting of the grasses and the small grain cereals.

Typically this method is carried out as follows:

A suitable amount of actively-growing callus or of suspension culture cells (normally from 1 to 40 days, preferably 2 to 10 days after subculture) is dispersed in a suitable liquid medium. Such suitable media include but are not limited to SH-O, SH-30 or SH-45 media, OMS, KM-8p, RY-2, mannitol, sucrose, or other sugar or sugar-alcohol solutions, a solution of an amino acid (for example, L-Proline) or even water. Preferable is a medium suitable for growth of the cells, or a solution of a sugar or sugar-alcohol in water. Typically, 0.01 to 0.1 g of callus is dispersed in every ml of liquid medium and then cooled on ice. Suitable cryoprotectant solutions, typically are mixture of osmotically active components and DMSO in water. When they are added to the pre-cooled dispersion of step (b) they normally are also pre-cooled on ice but can also can have higher temperatures up to about room temperature. The temperature of the cryopreserving solution is not critical. Representative cryoprotectant solutions include but are not limited to 0.5 to 2M Glycerol, 0.5 to 2M L-Proline, 0.5 to 4M Dimethyl Sulfoxide (DMSO) in water, pH 5.6, or 0.5 to 2M Glycerol, 0.5 to 2M Sucrose and 0.5 to 4M DMSO in water at pH 5 to 7. Other suitable components for cryoprotectant solutions include sugars and sugar alcohols, amino acids, and polymers such as PEG. Cryoprotectant solutions containing DMSO are preferably freshly prepared before each use or may be stored frozen. Other cryoprotectant solutions may be prepared some time before use, but are preferably prepared fresh or frozen.

Cryprotectant solution is typically added to the solution over a period of 1 second to 4 weeks, preferably, 1 second to 1 day, more preferably, 1 second to 1 hour. The cells are exposed to the cryoprotectant solution for a suitable period of time on ice, preferably 1 minute to 2 days, more preferably 10 minutes to 6 hours, most preferably 30 minutes to two hours. During or after this time, aliquots are distributed into suitable sterile cryopreservation vials or any other suitable vessel and usually kept on ice.

The vials are immersed at the surface of a liquid bath which is preferably at a temperature of between 0° and 4° C. The bath may consist of ethanol or any other suitable coolant. The bath is normally equipped with a stirring device to keep the coolant mixed, and is connected to an apparatus which can refrigerate the coolant at a controlled rate. This immersion step is not absolutely necessary but in certain cases can be of advantage.

Once the vials are in the coolant, the temperature is reduced at a suitable rate. A suitable rate can be in the range of 0.01° to 20° C. per minute, preferably 0.1° to 5° C. per minute, more preferably 0.2° to 2° C. per minute, most preferably 0.5° to 1° C. per minute. When the temperature reaches a low temperature, typically in the range of −20° to −60° C., preferably between −35° and −50° C., most preferably between −380° and −44° C., the vials are shock-frozen, for example, by plunging them into liquid nitrogen or liquid air. The optimum temperature for plunging them into liquid nitrogen or liquid air can vary with different cultures but is generally between −20° and −50° C. and can easily be determined by a person scilled in the art. The vials are then stored in liquid nitrogen or liquid air, either in the liquid itself or in the vapor above it, at a temperature not to exceed −100° C.

With some cultures it may be helpful to maintain the temperature at some steady low temperature for a certain period of time instead of immediately plunging into liquid nitrogen as the optimum temperature is reached.

In order to recover viable cell cultures, vials containing the callus material are removed from the liquid nitrogen. The vial is thawed, typically, with rapid agitation in a warm water bath at about 10° to 50° C., preferably 35° to 40° C., until all the ice has melted. Surprisingly, it has been found that vials of cryopreserved cells Pooideae family can be thawed by leaving them in air at room temperature until all the ice has thawed. The vials may then be kept on ice for a period of few seconds to 60 minutes, more preferably 1 to 10 minutes before being placed on culture medium.

The contents of the vial are spread onto a suitable solidified culture medium. Typically, 0.5 ml of thawed culture is spread onto each 10 cm diameter petri plate containing 30 to 50 ml of medium. The solid medium may be poured on a slant or a cavity scooped out of the medium around its periphery in order to aid the drainage of remaining cryoprotectant away from the cells. The cells may be washed one or more times with liquid culture medium, or other suitable solution, for example, a sugar or sugar alcohol solution, or a solution of an amino acid, before being placed on the culture medium.

The petri dishes are incubated on the medium in the dark at 27° C., as described for embryogenic callus above. Callus is then subcultured as for normal embryogenic callus as described above.

Step B: Isolation and Purification of Protoplasts Capable of Being Regenerated into Plants Including Fertile Plants Protoplasts are prepared from the embryogenic suspension cultures resulting from step A above. The isolation and purification is carried out by isolating embryogenic cell clusters from the suspension culture medium, for example, by filtering the suspension culture of step A on a Nalgene® 0.2 µm filter unit, and incubating the resultant cell clusters with a suitable enzyme preparation capable of removing the cell walls without harming the protoplasts. The enzyme is used as a filter-sterilized solution. All culture manipulations are carried out under sterile conditions using sterile materials. A suitable enzyme preparation may consist, for example, of about 2% (w/v) of cellulase RS in 7 mM $CaCl_2.H_2O$, 0.7 mM $NaH_2PO_4.H_2O$, 3 mM MES [pH 5–7] and glucose (to 550 mOs/kg $H_2O$). Usually the mixture is gently shaken on an orbital shaker at about 50 rpm in dim light (about 5 $\mu E/m^2 sec$) but this is not critical. The digestion is continued between 0° and 50° C., preferably between 10° and 35° C., most preferably between 26° and 32° C., and until protoplasts are released. The time required for digestion is typically between several seconds and 2 days, preferably between 1 hour and 1 day, most preferably between 3 and 5 hours.

The protoplasts released are collected and cleaned by standard methods such as filtration, centrifugation and washing.

At this stage a flotation step may be included. In this case the washed protoplasts are layered on top of a suitable medium, such as KM-8p culture medium made 700 mOs/kg $H_2O$ with sucrose, other suitable media as described in George E. F. et al. (eds), Exegetics Ltd., Edington, Westbury, Wiltshire, England (1987).

After centrifugation for about 10 minutes at about 60 g protoplasts banding at the interface are collected. Finally the protoplasts can be resuspended in the same culture medium and filtered, for example, by passing them through a stainless steel mesh screen (20 µm mesh size).

Contamination with whole undigested cells of the protoplast preparation not floated on sucrose is about 0.001 to 0.01% of the total. With the sucrose flotation step included the cell contamination is minimal. However, the sucrose flotation step results in a significant loss of those protoplasts with the densest cytoplasm. Consequently, plating efficiencies can decrease up to 10-fold when the flotation step is included. The protoplasts can also be purified using other methods known in the art, such as flotation on a sucrose solution, or other suitable buffered high density media, such as Percoll®.

Protoplast yields and subsequent plating efficiencies are optimal if the suspension cultures used for protoplast isolation are subcultured 1 to 30 days, preferably 5 to 10 days, previously.

The enzyme mixture characterized above is a modification of that described by Lu, Ch., et al. [Z. Pflanzenphysiol., 104 (1981) 311–318], and is found to be superior to other mixtures tested, giving yields of 40 to $70 \times 10^6$ protoplasts per gram fresh weight. Alternatively, however, 2% (w/v) of cellulase RS in KM-8p culture medium or other suitable medium such as those described in George E. F. et al. (eds), Exegetics Ltd., Edington, Westbury, Wiltshire, England (1987) also gives respectable yields of protoplasts. Glucose is clearly superior to sucrose and somewhat superior to mannitol as the osmoticum used during the isolation of protoplasts with regard to yield and subsequent plating efficiency. Other suitable enzyme mixtures known in the art may also be used.

The protoplasts obtained after filtration, for example, after passage through a 20 µm screen average 12 to 15 µm in diameter and are densely cytoplasmic.

Hence, the present invention provides a method of producing protoplasts of graminaceous plants of the subfamily Pooideae, which protoplasts are capable of being regenerated into plants, preferably into fertile plants. This method comprises:
(a) isolating tissue from suitable parts of graminaceous plants of the subfamily of the Pooideae, preferably the basal parts of young inner leaves, immature sexual embryos, immature inflorescences, mature seeds or seedling tissue, most preferably the youngest inner leaves,
(b) culturing this tissue in a medium capable of inducing the formation of embryogenic callus and of embryos,
(c) periodically subculturing the embryogenic callus and embryos on fresh medium capable of sustaining continuous proliferation,
(d) isolating embryogenic cell clusters after 0 to 500 transfers, preferably after 0 to 100 transfers, more preferably after 3 to 50 transfers, most preferably after 6 to 8 transfers, and
(e) removing the cell walls with suitable enzyme mixtures and isolating the resultant protoplasts.

A further embodiment of the invention embraces protoplasts (including the plant cells after regeneration of the cell walls) of graminaceous plants of the subfamily Pooideae capable of being regenerated into plants, especially fertile plants. Preferred are protoplasts or cells either derived from cell cultures or from embryogenic cell suspensions.

Step C: Establishment of Protoplast Cultures and Growth of Callus Capable of Being Regenerated into Plants and Fertile Plants The purified protoplasts of step B above are plated with or without treatment with exogenous DNA in a suitable liquid or a solidified medium. (The treatment with exogenous DNA will be described in detail in a subsequent paragraph.) Some suitable media include those based on KM-8p; RY-2; CC [Potrykus, I., et al., Theor. Appl. Genet.,54 (1979) 209–214]; and SH-30 and SH-45, with appropriate concentrations of sugars and plant growth regulators. The preferred media are KM-8p and SH-45 containing a solidifying agent. The preferred solidifying agent is agarose, especially Sea-Plaque® agarose [FMC Corp. Marine Colloids Division, P.O.Box 308, Rockland, Me. 04841, USA]. Where used, the concentration of SeaPlaque® agarose may be between 0.1 and 2.5% (w/v), preferably between 0.6 and 1.5% (w/v).

The plating of protoplasts on an agarose medium can be carried out in accordance with the methods described by: Shillito, R. D., et al. [Plant Cell Reports, 2 (1983) 244–247]; or in the European Patent Application EP-0,129,688 (Shillito, R. D., et al.); or by Adams, T. L., et al. [Plant Cell Reports, 2 (1983) 165–168]. These publications are incorporated by reference.

The medium in which the protoplasts are cultured may contain suitable substances to assist the protoplasts to divide and form colonies. These substances include 2,4-D, dicamba, picloram, or other plant growth regulators. Suitable plant growth regulators are known in the art. The concentration of such substances is usually in the range of 0.01 to 100 mg/liter.

Salicylic acid and its derivatives may promote division of, and/or colony formation from, Pooideae protoplasts. The derivatives of salicylic acid include but are not limited to O-acyl and O-aryl derivates. The O-acyl derivates include but are not limited to the short chain acyl groups, such as those having 1 to 7, preferably 1 to 4, and most preferably 2 to 3 carbon atoms. The O-aryl derivatives include but are not limited to those having one ore more 5 or 6 membered rings, which may be fused or unfused. The rings may be unsubstituted or substituted with one or more groups including alkyl having 1 to 5 carbon atoms, O-alkyl having 1 to 4 carbon atoms, halogen (especially chlorine and bromine), nitro-, amino-, and amino substituted by alkyl having 1 to 4 carbon atoms.

The derivatives of salicylic acid also include the carboxylate esters. The preferred carboxylate esters are the aryl, and alkyl esters wherein the alkyl group has 1 to 4 carbon atoms.

The derivatives of salicylic acid, in addition, include compounds wherein the salicylic acid ring is further substituted by, for example, one or more groups including alkyl having 1 to 4 carbon atoms, O-alkyl having 1 to 4 carbon atoms, halogen (especially chlorine and bromine), nitro-, amino-, and amino substituted by alkyl having 1 to 4 carbon atoms.

Preferred compounds promoting the division of, and/or the colony formation from, Pooideae protoplasts and cells are: O-acetoxybenzoic acid (aspirin, acetylsalicylic acid); O-hydroxybenzoic acid (salicylic acid); O-methoxybenzoic acid (methylsalicylic acid); and O-dimethylcarbamoylbenzoic acid) [O-(CO-dimethyl)-salicylic acid].

The concentration of the salicylic acid or a derivative thereof in the culture medium is suitably in the range of 0.1 to 3000 mg/liter, preferably in the range of 10 to 300 mg/liter, and most preferably about 100 mg/liter.

The medium in which the protoplasts are cultured may contain medium which has previously been conditioned by the growth of suitable cells such as, for example, *Zea mays*, *Dactylis glomerata* or other Gramineae, or even other (dicotyledoneous) plants. Preferred is medium in which an embryogenic suspension of a graminaceous species has been grown. Most preferred is medium in which an embryogenic suspension of *Dactylis glomerata* has been grown. The conditioned medium may be in the proportion of between 0 and 100% (v/v), preferably between 5 and 50% (v/v), more preferably between 30 and 40% (v/v) of the total medium.

The protoplasts may be cultured in the solid or liquid medium without subculture for a period of up to 12 weeks, preferably up to 6 weeks, most preferably in the range of 1 to 3 weeks. In a preferred embodiment of the present invention a solid medium can be placed in a liquid medium, as described in EP-0,129,688 (Shillito, R. D., et al.) or treated in some other manner to assist division of, and/or colony formation from the protoplasts.

The protoplasts are cultured in the light or, preferably in the dark at a temperature range between 0° and 50° C., preferably between 20° and 32° C., most preferably between 25° and 28° C. The light intensity is typically between 0.1 and 200 $\mu E/m^2 sec$, preferably between 30 and 90 $\mu E/m^2 sec$.

Plating efficiencies obtained using KM-8p medium vary from 0.5 to 10% depending on the quality of the protoplast preparation. The addition of 30 to 40% (v/v) conditioned suspension culture medium (suspension culture medium conditioned by growth of cells therein and made up to 550 mOsm/kg $H_2O$ by addition of glucose) to the protoplast culture medium does not result in a significant increase in plating efficiency but does accelerate the division process in the young protoplast-derived colonies.

In a preferred embodiment of the present invention the protoplasts are plated in an agarose solidified medium. The first cell divisions are noticed about two days after plating of the protoplasts. Subsequent divisions occur every 2 to 3 days. The process is not synchronous, as shown by the fact that first divisions can still be observed after 7 days. After 5 to 20 days, preferably after 10 to 14 days, after plating, the agarose solidified medium is cut into segments and the segments containing the cell colonies are transferred to a liquid nutrient medium. This procedure is known in the art as 'bead culture technique' and is fully described by Shillito, R. D., et al. [Plant Cell Reports, 2 (1983) 244–247; and in EP-0,129,688 (Shillito, R. D., et al.)]. Instead of cutting the agarose solidified medium it is also possible to liquefy the agarose medium and to transfer the liquefied medium to the liquid nutrient medium. This modification can be carried out in accordance with Adams, T. L., et al., supra. In both cases (cutting or liquifaction) the liquid component can remain KM-8p medium with glucose or sucrose with good colony growth observed. However, the optimal liquid component with regard to the growth rate is SH-45 medium with 4 g/liter casein hydrolysate. Within about 2 to 3 weeks of initiating the bead cultures, new suspension cultures can be observed in the plates. Microscopic examination of the agarose slabs reveals that normally some of the colonies closest to the surface grow out into the liquid and release small masses of cells while still anchored in the agarose. The new suspensions multiply rapidly and after another two weeks are transferred as suspension cultures in the usual manner or plated onto SH-30 plates for callus development. Alternatively the agarose can be spread on agarose solidified plates of SH-45 medium, and colonies allowed to grow out.

Hence, the present invention also relates to a method of producing cell cultures (suspension cultures or callus cultures) from protoplasts of graminaceous plants of the subfamily of the Pooideae, which cell culture is capable of being regenerated into plants, including fertile plants. This process comprises:

(a) culturing in a suitable culture medium protoplasts of graminaceous plants of the subfamily Pooideae capable of being regenerated into plants until they form cell colonies, and (b) culturing said cell colonies or parts thereof on a medium suitable to promote cell culture formation, and (c) isolating the resultant cell culture.

Step (b) is not absolutely necessary. It is also possible to let the protoplasts stay in the medium of step (a) until cell culture or embryos are formed.

A preferred embodiment of the present invention comprises plating the protoplasts on an agarose solidified medium, liquefaction or segmentation of the agarose solidified medium, transferring the liquefied or segmented medium to a liquid nutrient medium, and culturing until cell colonies are formed.

Preferred is a method wherein the parts of the cell colonies mentioned above under step (b) arise from cells and/or cell masses released to the liquid nutrient medium.

The callus and suspension cultures produced in this and other steps may be cryopreserved as described in step A.

Step D: Regeneration of Plantlets from Callus

Callus derived from protoplasts [step C], preferably friable granular callus, is subcultured one or more times, preferably every two weeks, onto a suitable fresh medium so as to induce embryo formation. Suitable inducing media include SH medium with appropriate concentrations of sugars and plant growth regulators.

Any embryos which are formed are removed and plated on a medium suitable to induce them to mature and germinate. Suitable media include SH-30 or OMS medium containing modifications to contain the appropriate amounts of sugars and plant growth regulators. The plates are placed in the light [10 to 200 µE/m²sec from cool white fluorescent lamps or from a mixture of daylight and Gro-lux® (Sylvania) fluorescent lamps (or any other suitable fluorescent lamp)]. Mature embryos are observed about 2 to 5 weeks after plating. In some cases one or more extra transfers to fresh medium can be beneficial for completing embryo maturation. The embryos differentiate further to form plantlets after a suitable period of time, typically 1 week to 6 months, more typically 1 to 3 months.

Alternatively, callus derived from protoplasts [step C], preferably friable granular callus, is subcultured one or more times, preferably every two weeks, onto a suitable fresh medium so as to induce embryo formation and maturation. Suitable media include but are not limited to OMS medium with appropriate concentrations of sugars and without plant growth regulators. The plates are placed in the light [10 to 200 µE/m²sec from cool white fluorescent lamps or from a mixture of daylight and Gro-lux® (Sylvania) fluorescent lamps (or any other suitable fluorescent lamp)]. The embryos differentiate further to form plantlets after a suitable period of time, typically 1 week to 6 months, more typically 1 to 3 months.

Step E: Obtaining Plants, Preferably Fertile Plants, from Plantlets

Plantlets obtained in accordance with step D above are transferred to a suitable medium such as for example SH-0 or OMS, which contain no growth regulators. Alternatively, a growth regulator stimulating root or shoot growth may be added. Suitable growth regulators are known in the art. The plantlets are cultured on said medium until they form roots. It is important to remove all callus from the plantlets, since this newly formed callus is found to be inhibitory to the growth of the plantlets. To this end the plantlets can be washed with sterile distilled water upon transfer. Callus which arises subsequently must be removed at regular intervals, preferably every 3 to 30 days, more preferably every 1 to 2 weeks. The time required for root formation is typically about 1 to 4 weeks, typically about 2 weeks. Plantlets with a good root system can be transferred to soil in the greenhouse and hardened off gradually. A sufficient length for the roots at this stage is in the range of 1 to 10 cm, more typically 2 to 5 cm, and for the shoot is in the range of 1 to 10 cm, more typically 2 to 5 cm. Alternatively, the plantlets can be subcultured indefinitely in-vitro by separation of the tillers and placing the plantlets on fresh medium such as SH-0 or OMS.

Thus, the inventive method of regenerating graminaceous plants, preferably fertile plants, of the subfamily Pooideae from callus comprises
(a) culturing callus of Pooideae plants, which callus is derived from protoplasts and is capable of being regenerated into plants on a medium capable of inducing embryo formation until embryos are formed,
(b) culturing the embryos on a medium suitable to induce them to mature and germinate, and (c) culturing the resultant plantlets until sufficiently developed to be transferred to soil to form mature plants.

Flowering can be induced as described by Heide, [Physiol. Plantarum., 70 (1987) 523–529] or as appropriate for the particular species or variety being used. Methods for inducing flowering are known in the Pooideae. Seed produced from these plants can be treated in an appropriate way to induce germination, and sown either in pots or sterilized and plated on Murashige and Skoog medium without growth regulators (OMS medium) and solidified with 0.8% agar or agarose, or GelRite® or any other suitable gelling agent. The seed can also be sown on medium containing between 10 and 1000 µg/ml hygromycin B to determine the inheritance of the hygromycin resistance character.

Thus, the inventive method of regenerating fertile graminaceous plants of the subfamily Pooideae from callus comprises
(a) culturing callus of Pooideae plants, which callus is derived from protoplasts and is capable of being regenerated into fertile plants on a medium capable of inducing embryo formation until embryos are formed,
(b) culturing the embryos on a medium suitable to induce them to mature and germinate,
(c) culturing the resultant plantlets until sufficiently developed to be transferred to soil to form mature plants, and
(d) obtaining seed following controlled or open pollination.

Step F: Treating the Protoplasts with Exogenous DNA

Pooideae protoplasts may be treated with exogenous DNA so as to produce cells that contain all or part of the exogenous DNA stably integrated into their genetic material. exogenous DNA is any DNA added to a protoplast. It may be homologous or heterologous to the plant being transformed. The Exogenous may contain a promoter active in graminaceous plants, preferably in plants of the subfamily Pooideae, or may utilize a promoter already present in the plant genome. The exogenous DNA may contain one or more genes which alter the genotype and especially the phenotype of the resultant cells or of the plants being regenerated from transformed cells. It is desired, however, that the genetic sequence coding for one or more desired proteinaceous products be expressed, and produces one or more functional enzymes or polypeptides in the resulting cell and plant respectively. The exogenous DNA may be a chimeric gene, or a portion thereof.

Treatment of the protoplasts with exogenous DNA can be carried out by methods such as those described in the following publications: [Paszkowski, J., et al. The EMBO Journal 3, No.12 (1984) 2717–2722; European Patent Application EP-0,164,575, (Paszkowski, J.,et al.); Shillito, R. D., et al., Bio/Technology, 3 (1985) 1099–1103; Potrykus, I., et al., Mol. Gen. Genet., 199 (1985) 183–188; Loerz, H., et al., Mol. Gen. Genet., 199 (1985) 178–182; Fromm, M. E., et al., Nature, 319 (1986) 791–793; British Patent Application GB-2,140,822 (Mettier, I. J.); and Negrutiu, I., et al., Plant Mol. Biology, 8 (1987) 363–373]. These publications are incorporated by reference.

The exogenous DNA may be added in any form such as, for example, naked linear or circular DNA, DNA encapsulated in liposomes, DNA in sphaeroplasts, DNA in other plant protoplasts, DNA complexed with salts, etc. Uptake of foreign DNA may be stimulated by any suitable method known in the art including the methods described in the references quoted above.

Primarily, the chimeric genes contemplated in this invention are those which provide the transformed plant protoplasts, protoplast-derived tissues and finally the protoplast-derived plants with valuable properties, such as increased resistance to pathogens (e.g. to phytopathogenic fungi, bacteria, viruses, etc.); resistance to chemicals [e.g. to herbicides (such as triazines, sulfonylureas, imidazolinones, triazolo-pyrimidines, bialaphos, glyphosate, etc.), insecticides or other biocides]; resistance to cytotoxins (e.g. to hygromycin, kanamycin, chloramphenicol, etc.); resistance to adverse environmental (edaphic or atmospheric) influences (e.g. to heat, cold, wind, soil conditions, moisture, dryness, etc.); or with increased formation of reserve or storage substances in the leaves, seeds, tubers, roots, stalks, etc. Desirable substances produced by a transgenic plant include proteins, starches, sugars, amino acids, alkaloids, flavors, colors, fats, etc.

Resistance to cytotoxins may be conferred by a gene expressing in the plant cells an enzyme that detoxifies the cytotoxin, for example, neomycin phosphotransferase type II or aminoglycoside phospotransferase type IV for detoxification of kanamycin, hygromycin and other aminoglycoside antibiotics, or a glutathione-S-transferase or cytochrome P-450 or other catabolic enzyme known to detoxify triazine, sulfonylurea or other herbicides. Resistance to cytotoxins may also be conferred by a gene that expresses in a plant a form of a "target enzyme" (site of the action of the cytotoxin) which is resistant to the cytotoxin, for example, a form of aceto hydroxy acid synthase which is insensitive to inhibition by sulfonylureas or imidazolinones, or other herbicide acting at this metabolic step, or a form of EPSP synthase that is insensitive to inhibition by glyphosate. It can be advantageous to express these altered target enzymes in a form that allows their transport in the plant cell into the correct cellular compartment, i.e. the chloroplast in the above examples.

In certain cases it is advantageous to target the gene products into the mitochondria, the vacuoles, into endoplasmatic vesicles, or other cell parts or even into the intercellular (apoplastic) spaces.

Resistance to certain classes of fungi may be conferred, for example, by the introduction of a gene that expresses chitinase in the plant tissues. Many plant pathogenic fungi contain chitin as an integral part of hyphal and spore structure, e.g. basidiomycetes (smuts and rusts) and ascomycetes and fungi imperfecti (including Alternaria and Bipolaris, *Exerophilum turcicum,* Colletotricum, Gleocercospora and Cercospora). Chitinase can inhibit the growth of mycelia of certain pathogens in vitro. A plant leaf or root expressing chitinase constitutively or in response to a pathogen invasion is protected against many types of fungal attack. Constitutive expression may or may not be advantageous over the inducible expression that is normal response to pathogen attack in certain plants, because the chitinase is present immediately at high level with no lag time required for de novo synthesis.

Insect resistance may, for example, be conferred by a gene encoding a polypeptide that is toxic to insects or their larvae, such as the crystalline protein of *Bacillus thuringensis* [Barton, K. A., et al., Plant Physiol., 85 (1987) 1103–1109; Vaeck, M., et al., Nature, 328 (1987) 33–37]. A second class of protein which will confer insect resistance are protease inhibitors. Protease inhibitors are common constituents of plant storage structures [Ryan, C., Ann. Rev. Plant Physiol. 24 (1973) 173–196]. Purified Bowman-Birk protease inhibitor isolated from soybean has been shown to inhibit gut protease of *Tenebrio larvae* [Birk, Y., et al., Biochim. Biophys. Acta 67 (1963) 326–328]. The gene encoding cowpea trypsin inhibitor is described by Hilder et al. [Nature, 330 (1987) 160–163]. A gene encoding a protease inhibitor may be placed under the control of a plant promoter, preferably a constitutive promoter such as the CaMV 35S promoter (which is described by Odell, J. T. et al., Nature, 313, (1985) 810), in a suitable vector. The gene, for example, the coding sequence for the soybean Bowman-Birk protease inhibitor, may be obtained using the cDNA cloning methods described by Hammond et al. [J. Biol. Chem., 259 (1984) 9883–9890]. An alternative method of obtaining a gene for protease inhibitors with less than 100 amino acids, such as the lima bean trypsin inhibitor, is to synthesize it. The coding sequence is predicted by back-translation and restriction sites appropriate for the desired vector included at each end. The synthetic gene is prepared by synthesizing overlapping oligonucleotides of 30 to 60 bases. The fragments are kinased, ligated [Maniatis et al. supra] and cloned into the appropriate vector. A clone whose insert is in the correct orientation may be identified by sequencing. Plasmid DNA is isolated and used for incorporation into the protoplasts [Abel, P. P., et al., Science, 233 (1986) 738.

Also included in the present invention are genes coding for pharmaceutically active ingredients, for example, alkaloids, steroids, hormones and other physiologically active substances, and flavins, vitamins and colorings. Therefore, genes which are contemplated in this invention include, but are not limited to, plant specific genes, such as the zein gene [Wienand, U., et al., Mol. Gen. Genet., 182 (1981) 440–444] mammalian specific genes, such as the insulin gene, the somatostatine gene, the interleukine gene, the t-PA-genes [Pennica, P., et al., Nature, 301 (1983) 214] etc., or genes of microbial origin, such as the NPT II gene as well as genes of synthetic origin such as the insulin gene [Itakura, K., et al., J. Am. Chem. Soc. 97 (1975) 7327].

In a preferred embodiment of the present invention the Pooideae protoplasts are transformed by means of a combination of electroporation and polyethylene glycol treatment. Immediately after the purification of the protoplasts obtained in step B, electroporation is performed as described by Shillito, R. D., et al. [Bio/Technology 3 (1985) 1099–1103, or in EP-0,164,575 (Paszkowski, J., et al.)]. The protoplasts are resuspended in an electroporation buffer after the last wash. Suitable electroporation buffers include aqueous solutions of mannitol containing an appropriate amount of $MgCl_2$. An aqueous solution of DNA is added. In one embodiment the DNA is plasmid pCIB709 linearized by treatment with a suitable restriction endonuclease. The resulting mixture is gently mixed. In one embodiment, one half volume of a 24% (w/v) solution of PEG in 0.5M mannitol and 30 mM $MgCl_2$ is added. After mixing the protoplasts are transferred to the chamber of a Dialog® Electroporator [DIA-LOG G.m.b.H., Haffstrasse 34, D-4000 Duesseldorf 13, FRG], and 2 to 5 pulses, preferably 3 pulses of about 2,000 to 5,000 V/cm initial voltage and exponential decay constant of 10 μsec applied at 30 sec intervals. The sample is then placed in a petri plate and 1 to 25% of agarose as solidifying agent is added, the protoplasts distributed throughout the medium, and the agarose allowed to set. From this culture of transformed protoplasts transgenic Pooideae plants, including fertile transgenic Pooideae plants, are regenerated as described under steps C to F above.

In a further preferred embodiment of the present invention, Pooideae protoplasts are transformed according to the method described by Negrutiu, I., et al. supra. In this case the purified protoplasts are suspended following the last wash in 0.5M mannitol containing between 15 and 45 mM MgCl$_2$. DNA is added in an aqueous solution, and then an equal volume of a 36% solution of PEG is added [Negrutiu et al. supra]. The resulting mixture is gently mixed and incubated for 5 to 60 minutes, preferably for about 30 minutes, at temperatures between 10° and 32° C., preferably at room temperature (about 25° C.). During incubation the mixture is occasionally shaken. After incubation the protoplasts are washed and plated on a suitable culture medium. Suitable culture media include but are not limited to KM-8p medium containing 0.3 to 2.5% (w/v) agarose, preferably 0.6 to 2% (w/v) agarose as a solidifying agent. The transformed protoplasts are distributed throughout the medium, and the agarose is allowed to gel. From this culture, transgenic, Pooideae plants, including fertile Pooideae plants are regenerated in accordance with steps C to E above.

A preferred exogenous DNA is the plasmid pCIB709 as shown in sequence 1, in its linearized form.

Step G: Selection of Transformed Colonies

The agarose solidified medium [step F] containing the transformed protoplasts is incubated in the light or preferably in the dark for 5 to 30 days, preferably for 8 to 15 days, more preferably for 10 days, at a temperature range between 0° and 50° C., preferably 20° and 32° C., more preferably 25° and 28° C. The solidified medium is cut into, for example, 5 slices and selected in the 'bead type' culture system in accordance with the methods described by: Shillito, R. D., et al. [Plant Cell Reports, 2 (1983) 244–247]; or in the European Patent Application EP-0,129,688 (Shillito, R. D., et al.); or in Shillito, R. D., et al. [Bio/Technology 3 (1985) 1099–1103, or in European Patent Application EP-0, 164,575 (Paszkowski, J., et al.)]. Number and size of the slices are not critical. In one embodiment, four of these slices are put separately into a suitable medium, such as, for example, SH-45 culture medium containing 4 g/liter casein hydrolysate and 20–100 μg/ml hygromycin B. The fifth slice is put into the same medium but without hygromycin B (control).

After about 4 to 5 weeks the putative transformed cell colonies are cut out of the agarose and cultivated in suitable culture medium, such as SH-45 containing 20–100 μg/ml hygromycin B, which is agitated at, for example, 50–80 rpm on an orbital shaker. After another 4 to 5 weeks all colonies which make a new suspension culture are transferred to new medium containing 20 μg/ml hygromycin B. The new suspensions are grown for a minimum of two subcultures in the presence of 20 μg/ml hygromycin B and incubated under the same conditions as described above until callus is formed.

Callus and suspension cultures, and cultures derived from the materials produced in this step may be cryopreserved as described in step A.

Step H: Regeneration of Transformed Pooideae Plants from Callus

Transformed Pooideae plants are regenerated from transgenic callus of step G in accordance with the procedure described under steps D to E above.

UTILITY

The method of the present invention permits protoplasts of graminaceous plants of the subfamily Pooideae to be regenerated into plants, and more preferably, fertile plants. This possibility enables one to introduce exogenous DNA stably into the genome of such plants, and to alter their geno- and phenotypes. In addition the protoplasts can be fused with protoplasts from the same or another species, in order to produce novel combinations of nuclear DNA, or novel combinations of nuclear and organelle DNA. Moreover, the protoplasts can be used as a source of clonal material, on which mutagenesis and/or selection for a desired phenotype can be carried out.

Examples of desired phenotypes include resistance to toxic concentrations of natural or synthetic chemicals including but not limited to insecticides, herbicides, fungicides, bactericides, heavy metals, salts, pathotoxins, metabolic inhibitors, structural or functional analogs of cellular metabolites. Other examples of desirable phenotypes which can be selected for include resistance to adverse environmental conditions such as cold or warm temperatures or to biotic agents such as pathogens.

The following experiments and examples further illustrate the present invention in detail but are not to be construed to limit the scope thereof.

EXAMPLES

Example 1: Preparation of Embryogenic Suspensions from Tissue of *Dactylis glomerata L.* (Orchardgrass)

Embryogenic callus is initiated from basal sections of the youngest leaves of greenhouse-grown orchardgrass plants (*Dactylis glomerata L.*) as described by Hanning, G. E. et al. [Theor. Appl. Genet., 63 (1982) 155–159]. The leaves are surface sterilized by immersion in a 1:10 dilution of Clorox solution [A solution of 5.25% (w/v) Sodium hypochlorite; The Clorox Company, Oakland, Calif.94623, USA] for about 10 minutes and then cut aseptically into small segments of 1 to 5 mm in length or in diameter. These segments are plated on sterile SH-30 medium containing 0.8% (w/v) agarose as a gelling agent. Callus and/or embryogenic structures appear within 2 to 6 weeks after plating, upon culture at about 25° C. Embryogenic callus was maintained by subculturing onto fresh SH-30 medium every 2 to 4 weeks and culturing in the dark at 25° C.

Embryogenic suspension cultures are initiated by placing approximately 0.5 g fresh weight of embryogenic callus into 50 ml of liquid medium described by Gray, D. J.,et al. [Plant Cell Tissue Organ Cult., 4 (1985) 123–133] containing 45 μM dicamba and 4 g/liter casein hydrolysate. The suspension cultures are grown at 27° C. under a 16 hours light (40 μE/m$^2$sec), 8 hours dark photoperiod on a gyratory shaker at about 130 rpm in 125 ml Delong flasks sealed with a metal cap and parafilm®. After approximately four weeks the large clumps are allowed to settle for about 30 seconds and 10 ml aliquots of the supernatant medium containing small cell clusters are removed and transferred to 50 ml of fresh medium. This process is repeated every 3 to 4 weeks using the most successful cultures as judged by smaller clump size and better quality based on the presence of small, cytoplasmic cells. After 5 to 8 transfers the suspensions are essentially free of non embryogenic cells and the majority of the embryogenic cell clusters are quite small (150 to 2000 μm).

Example 2: Isolation and Purification of *Dactylis glomerata L.* Protoplasts

Protoplasts are prepared from embryogenic suspension cultures of example 1 by aseptically filtering the cells on a Nalgene® 0.2 μm filter unit and then adding 0.5 g fresh weight cells to each 12.5 ml of protoplast enzyme mixture in a petri dish. The enzyme mixture consists of 2% (w/v) Cellulase RS, 7 mM $CaCl_2 \times H_2O$, 0.7 mM $NaH_2PO_4 \times H_2O$, 3 mM MES (pH 5.6), glucose (550 mOs/kg $H_2O$ of pH 5.6), and is filter sterilized. The mixture is swirled on an orbital shaker at about 50 rpm in dim (<5 $\mu E/m^2 sec$) light for about 4 to 5 hours. The digest is then sieved through a stainless steel sieve (100 μm mesh size) and distributed into 12 ml centrifuge tubes which are centrifuged at about 60 to 100 g for about 5 minutes. The protoplast-containing sediment is then washed three times with protoplast culture medium KM-8p adjusted to 550 mOs/kg $H_2O$ with glucose. At this point a flotation step may be included for further purification of the protoplasts. In this case, the washed protoplasts are layered atop 10 ml of KM-8p culture medium adjusted 700 mOs/kg $H_2O$ with sucrose. After centrifugation at 60 to 100 g for about 10 minutes, protoplasts banding at the interface are collected using a fine pipette. Finally, the protoplasts are resuspended in 1 to 2 ml KM-8p culture medium and sieved through a stainless mesh screen (20 μm mesh size). The protoplasts released are collected and washed and resuspended in KM-8p medium for culture or in osmotically adjusted medium suitable for transformation according to Example 6.

Example 3: *Dactylis glomerata L.* Protoplast Culture and Growth of Callus (a) The purified protoplasts are plated at a density of about $5 \times 10^5$ protoplasts/ml in KM-8p culture medium containing 1.3% (w/v) SeaPlaque® agarose [FMC Corp., Marine Colloids Division, Rockland, Me., USA] and 30 to 40% (w/v) of conditioned medium (obtained from 3 to 4 week-old *Dactylis glomerata L.* embryogenic suspension cultures by filtering the medium through a sterile Nalgene® 0.2 μm filter, making the medium 550 mOsm/kg $H_2O$ by addition of glucose, and again filter sterilizing). The plates are then placed in the dark at a constant temperature of 28° C. After 10 to 14 days the agarose is cut into wedges and placed into 'bead culture' as described by Shillito, R. D., et al. [Plant Cell Reports, 2 (1983) 244–247] using 20 ml SH-45 suspension culture medium with 3% (w/v) sucrose per 3 ml original agarose embedded culture. The plates are put on a platform shaker and agitated at about 50 rpm in light at 8 $\mu E/m^2 sec$. New suspension cultures are formed as the colonies grow out of the agarose and release cells into the liquid medium. The resultant suspension cultured cells are plated onto agar-solidified SH-30 medium and placed in the dark at 25° C. until callus is formed.

(b) Protoplasts are cultured as described in example 3(a) above except that the culture media contains an addition of 100 mg/liter O-acetyl-salicylic acid.

(c) Protoplasts are cultured as described in example 3(a) above except that the culture media contains an addition of 30 mg/liter O-acetyl-salicylic acid.

(d) Protoplasts are cultured as described in example 3(a) to 3(c) above except that the culture media contains no conditioned medium.

Example 4: Regeneration of *Dactylis glomerata L.* Plants from Protoplast-derived Callus a) *Dactylis glomerata L.* callus (obtained as described in Example 3) derived from protoplasts is grown on solidified SH-30 medium, and subcultured every two weeks. Any embryos which form are removed and plated on germination medium (SH-0) and placed in the light (45 to 55 $\mu E/m^2 sec$). Germination of these embryos occurs in 1 to 4 weeks and the resultant plantlets are placed on SH-0 medium in the light to form root systems. They are moved into the greenhouse at the six to twelve leaf stage, and hardened off gradually.

b) Callus (obtained as described in Example 3) derived from protoplasts is grown on SH-0 medium solidified with 0.24% (w/v) GelRite® in the light (45 to 55 $\mu E/m^2 sec$), and subcultured every two weeks. The resultant plantlets are placed on a 1:1 mixture of SH-0 and OMS media solidified with a combination of 0.12% (w/v) GelRite® and 0.4% (w/v) agar in the light to form root systems. They are moved to the greenhouse at the six to twelve leaf stage, and hardened off gradually.

c) Small plantlets are obtained as described in 4(a) and 4(b) above, and are placed on OMS medium solidified with 0.8% (w/v) agar in the light to form root systems. They are moved to the greenhouse at the six to twelve leaf stage, and hardened off gradually.

d) Small plantlets are obtained as described in 4(a) above and are placed on a 1:1 mixture of SH-0 and OMS media solidified with a combination of 0.12% (w/v) GelRite® and 0.4% (w/v) agar in the light to form root systems. They are moved to the greenhouse at the six to twelve leaf stage, and hardened off gradually.

Example 5: Construction of Plasmid pCIB709, an *E. coli* Replicon Bearing a Plant Expressible Hygromycin-resistance Gene [35S/Hyg$^r$]

The coding sequence for the structural gene encoding hygromycin-resistance is isolated from the plasmid pLG90 [Gritz, L. and Davies, J., Gene 25, (1983) 179–188] on a BamHI fragment approximately 1150 bases in size. The plasmid pLG90 is available from Linda Gritz [Applied Biotechnology, 80 Rogers St., Cambridge, Mass. 02141.] This BamHI fragment is inserted into the BamHI site of pCIB710 [Rothstein, et al., Gene 53, (1987) 153–161] to construct the plasmid pCIB709. The plasmid pCIB710 contains the regulatory regions of the CaMV [cauliflower mosaic virus] 35S transcript with the promoter and terminator region separated by a unique BamHI site. The resulting plasmid, pCIB709, has been deposited with ATCC, accession number 40428.

Before use in transformation, the plasmid pCIB709 can be linearized by treatment with restriction endonuclease Pvu II. This construct contains a hygromycin-resistance (aminoglycoside phosphotransferase type IV) gene together with the 5' and 3' expression signals of the CaMV 35S transcript from cauliflower mosaic virus (CaMV) in a pUC plasmid. The sequence of pCIB709 is given in sequence 7.

Example 6: Transformation of *Dactylis glomerata L.* Protoplasts by Means of Electroporation (a) Immediately after purification of the protoplasts, electroporation is performed according to Shillito, R. D., et al. [Bio/Technology, 3 (1985) 1099–1103] using the linearized plasmid pCIB709 as shown in sequence 7. The protoplasts are resuspended after the last wash at a density of about $7 \times 10^6$ protoplasts/ml in the electroporation buffer (0.4M mannitol, 6 mM $MgCl_2$). The protoplasts are placed in 0.7 ml aliquots in 10 ml plastic centrifuge tubes. Plasmid DNA (62 μl water containing pCIB709 restricted with Puv II and sonicated calf thymus DNA [Sigma] to give final concentrations of plasmid pCIB709 and calf thymus DNA of 10 μg/ml and 50 μg/ml respectively is added to the tubes. Then 0.38 ml polyethylene glycol (PEG) solution [24% (w/v) PEG 6000 in 0.4M mannitol 30 mM MgCl$_2$, 0.1% (w/v) MES (pH 5.6)] is added and the solution gently mixed. The protoplast suspension is transferred into the chamber of a Dialog® Electroporator and 10 pulses of 3250 V/cm initial voltage and exponential decay constant of 10 μsec applied at 30 sec intervals. The sample is removed from the chamber, and placed in a 10 cm diameter petri dish. 10 ml of KM-8p medium containing 1.2% (w/v) SeaPlaque® agarose is added, the protoplasts distributed evenly throughout the medium, and the agarose allowed to gel.

(b) Example 6(a) is repeated except that the initial voltage used is 3500 V/cm.

(c) Example 6(a) is repeated except that the initial voltage used is 4000 V/cm.

(d) Example 6(a) is repeated except that the initial voltage used is 5000 V/cm.

(e) Example 6(a) is repeated except that the initial voltage used is 3000 V/cm.

(f) Example 6(a) is repeated except that the initial voltage used is 2500 V/cm.

(g) Examples 6(a) to 6(f) are repeated except that PEG of MW 4000 is used.

(h) Examples 6(a) to 6(f) are repeated except that PEG of MW 8000 is used.

(i) Examples 6(a) to 6(h) are except that the final PEG concentration is between 10% and 30% (w/v).

(j) Examples 6(a) to 6(i) are repeated except that a heat shock as described in Shillito, R. D., et al., [Biotechnology, 3 (1985) 1099–1103] and Potrykus, I. et al. [Mol. Gen. Gent., 199 (1985) 183–188] is used.

Example 7: Transformation of *Dactylis glomerata L.* Protoplasts by Treatment with Polyethylene Glycol (PEG)

(a) PEG mediated direct gene transfer is performed according to Negrutiu, I., et al. supra. The DNA used is the linearized plasmid pCIB709.

The protoplasts are suspended following the last wash in 0.5M mannitol containing 15 mM MgCl$_2$ at a density of about $2\times10^6$ per ml. The protoplast suspension is distributed as 1 ml aliquots into 10 ml plastic centrifuge tubes. The DNA is added as described in example 6 above, and then 0.5 ml of the PEG solution added [40% (w/v) PEG 4000 in 0.4M mannitol, 0.1M Ca(NO$_3$)$_2$, (pH 7.0)]. The solutions are mixed gently and incubated for 30 minutes at room temperature (about 24° C.) for 30 minutes with occasional shaking. 1.4 ml of the wash solution is then added, and the contents of the tube gently mixed. The wash solution consists of 87 mM mannitol, 115 mM CaCl$_2$, 27 mM MgCl$_2$, 39 mM KCl, 7 mM Tris/HCl and 1.7 g/liter m-inositol, (pH 9.0). Four further 1.4 ml aliquots of wash solution are added at 4 minute intervals, with mixing after each addition. The tube is then centrifuged at about 60 g for about 10 minutes, and the supernatant discarded. The sedimented protoplasts are taken up in 1 ml KM-8p culture medium, and placed in a 10 cm petri dish. 10 ml of KM-8p medium containing 1.2% (w/v) SeaPlaque® agarose is added. The protoplasts are evenly distributed throughout the medium, and the agarose allowed to gel.

(b) Transformation is carried out as described in example 7(a) except that the pH of the wash solution is adjusted to 5.6.

(c) Transformation is carried out as described in example 7(a) except that the pH of the wash solution is adjusted to 7.0.

(d) Transformation is carried out as described in examples 7(a) to 7(c) except that the PEG used is PEG of MW 6000.

(e) Transformation is carried out as described in examples 7(a) to 7(c) except that the PEG used is PEG of MW 2000.

(f) Transformation is carried out as described in examples 7(a) to 7(c) except that the PEG used is PEG of MW 8000.

(g) Transformation is carried out as described in examples 7(a) to 7(f) except that heat shock as described in Shillito, R. D. et al., Biotechnology, 3 (1985) 1099–1103 is used.

(h) Transformation is carried out as described in examples 7(a) to 7(g) above except that the wash medium consists of 154 mM NaCl, 125 mM CaCl$_2$, 5 mM KCl, 5 mM glucose, pH to 6.0 with KOH.

(i) Transformation is carried out as described in examples 7(a) to 7(g) above except that the wash medium consists of 0.2M CaCl$_2$, 0.1% (w/v) MES, pH 6.0 with KOH.

(j) Transformation is carried out as described in examples 7(a) to 7(g) above except that the wash medium consists of 0.2M CaCl$_2$, 7 mM Tris/HCl, pH 9.0 with KOH.

Example 8: Transformation of *Dactylis glomerata L.* Protoplasts by Electroporation or PEG Treatment (a) Transformation is carried out as described in examples 6 and 7 except that the pCIB709 plasmid DNA is restricted with restriction enzyme Bgl I before being used for transformation.

(b) Transformation is carried out as described in examples 6 and 7 except that the pCIB709 plasmid DNA is restricted with restriction enzyme HindIII before being used for transformation.

Example 9: Transformation of *Dactylis glomerata L.* Protoplasts by Electroporation or PEG Treatment Transformation is carried out as described in examples 6, 7 or 8, except that the protoplasts are treated at 45° C. for about 5 minutes prior to distribution of the aliquots into tubes for transformation or after distribution of the aliquots, and before addition of the PEG.

Example 10: Selection of Transformed Colonies (a) The culture plates (petri dishes) containing the protoplasts are incubated for 10 days in the dark at about 25° C. and then cut into 5 equal slices for 'bead cultures' [Shillito, R. D., et al., Plant Cell Reports,2 (1983) 244–247]. 4 of the slices are placed each into 20 ml SH-45 culture medium with 4 g/liter casein hydrolysate and 20 μg/ml hygromycin B. The fifth slice is put into 20 ml of the same medium but without hygromycin B as a nonselected control. After 4 to 5 weeks the putative transformed protoplast-derived cell colonies growing in hygromycin B are cut out of the agarose and placed into a 19 mm petri dish with 2 ml of liquid SH-45 medium containing 20 μg/ml hygromycin B, which is agitated at about 50 rpm on an orbital shaker. After another 4 to 5 weeks all colonies which grow to make new suspensions are transferred into 125 ml erlenmeyer flasks and grown in a manner similar to the parent suspension culture, except that 20 μg/ml hygromycin B is included in the medium.

The new suspensions are subcultured every 1 to 3 weeks using SH-45 medium containing 4 g/liter casein hydrolysate and 20 μg/ml hygromycin B. Cells from these suspensions are also plated on solidified SH-30 medium containing 20 μg/ml hygromycin B and incubated at about 25° C. in the dark. Calli grown from the plated cells are subcultured every two weeks onto fresh medium. The cells which grow in the presence of hygromycin B are presumed to be transformants.

(b) Selection is carried out as described in example 10(a) except that the protoplast-derived cell colonies growing in hygromycin B—containing medium are placed on agar plates of SH-30 medium containing 20 µg/ml hygromycin B and incubated at about 25° C. in the dark.

Example 11: Regeneration of Transformed *Dactylis glomerata L.* Plants

Plants are regenerated from transformed callus as described in example 4 for non-transformed material.

Example 12: Extraction of DNA from Callus and Leaf Tissue

DNA is extracted from callus and leaves of regenerated plants using a modification of the CETAB method [Roger and Bendich, Plant Mol. Biology, 5 (1985) 69–76]. This method is described here for *Dactylis glomerata L.* but can be used as effectively on tissues of any other Pooideae plant. Other commonly used methods for DNA extraction can also be used to obtain DNA from this material.

Callus grown on SH-0 medium and SH-30 medium is frozen in dry ice, and then ground to a fine powder at liquid nitrogen temperature in a pestle and mortar. The resulting powder is transferred to a 5 ml polypropylene centrifuge tube pre-cooled to liquid nitrogen temperature (2 g powder per tube). Care is taken that the powder never thaws out during the procedure. The powder is freeze-dried overnight, and then distributed into 2.2 ml Eppendorf tubes, <0.5 ml powder per tube. 1 ml of CETAB extraction buffer is added to each tube, and they are incubated at 60° C. for about 30 to 45 minutes. The tubes are allowed to cool to room temperature, and 1 ml of chloroform/isoamyl alcohol (24:1) added. After mixing, the solution is centrifuged for about 30 sec at 3000 rpm in an Eppendorf centrifuge, and the water phase removed to a fresh tube. ¹/₁₀ volume of 10% (w/v) CETAB solution is added, and the chloroform extraction is repeated. The water phase is removed to a fresh tube, and an equal volume of precipitation buffer added. The DNA and RNA precipitate at room temperature. After a period of about 30 minutes to 1 hour to allow precipitation, the tubes are again centrifuged, and the supernatant discarded. The precipitates are resuspended in high salt TE buffer at 65° C. for about 30 minutes.

| | |
|---|---|
| CETAB extraction buffer: | 1% (w/v) CETAB |
| | Tris pH 8.0 (50 mM) |
| | EDTA (10 mM) |
| | NaCl (0.7 M) |
| | 0.5% (w/v) PVP Mol. Wt. 360,000 |
| | [PVP: polyvinylpyrrolidine] |
| 10% CETAB: | 10% (w/v) CETAB |
| | NaCl (0.7 M) |
| Precipitation buffer: | 1% (w/v) CETAB |
| | Tris pH 8.0 (50 mM) |
| | EDTA (10 mM) |
| High salt TE: | Tris pH 8.0 (10 mM) |
| | EDTA (1 mM) |
| | NaCl (1 M) |
| TE buffer: | Tris pH 8.0 (10 mM) |
| | EDTA (1 mM) |
| ¹/₁₀ TE: | Tris pH 8.0 (1 mM) |
| | EDTA (0.1 mM) |

Example 13: Purification of the DNA

The DNA prepared as in example 12 or any other suitable method can be purified by any of a number of known methods. Examples of suitable methods include but are not limited to: ethidium bromide CsCl gradient centrifugation, treatment with phenol/chloroform, and purification on a step gradient without ethidium bromide. Such methods are described in Maniatis et al., supra.

(a) Purification by Phenol/Chloroform Treatment

The nucleic acids from example 12 above are precipitated with 2 volumes of cold ethanol (−20° C.). The tubes are centrifuged for 2 to 3 minutes at 5000 g. The supernatant is removed and the precipitate washed with 70% ethanol and 100% ethanol. The nucleic acids are partially dried in the airstream from a sterile flow bench. The DNA is dissolved overnight in 200 µl of ¹/₁₀ TE buffer. The DNA solution is transferred to an Eppendorf centrifuge tube and 10 µl of a 2 mg/ml solution of RNAase (boiled previously to deactivate DNAase), is added and the tubes incubated at 37° C. for about 1 hour. 0.25 volume 5M NaCl are added and the DNA precipitated by adding 0.4 volume of 30% PEG (Mol. Wt. 6000 to 8000) containing 1.5M NaCl and standing the tube at −20° C. for about 1 hour. The tubes are centrifuged for 5 minutes, the supernatant removed, and the precipitate washed with cold absolute ethanol. After briefly drying in the air stream from a sterile flow bench, the pellet is resuspended in 0.3 ml TE buffer. The solution is extracted with Phenol/chloroform/isoamyl alcohol (25:24:1) equilibrated with TE buffer, centrifuged for 30 sec in an Eppendorf centrifuge, and the water phase transferred to a fresh tube. The solution is extracted with Chloroform/isoamyl alcohol (24:1), centrifuged for 30 sec, and the water phase removed to fresh tube. The chloroform extraction is repeated. A ¹/₁₀ volume of 3M sodium acetate is added, followed by 2 volumes of ice cold absolute ethanol to precipitate the DNA. The precipitate is collected by centrifugation, and washed with 70% and 100% ethanol, dried briefly in a stream of sterole air, and dissolved in sufficient TE buffer to obtain a solution at 0.25 to 1 µg/µl for use in Southern analysis.

(b) Purification on a Step Gradient without Ethidium Bromide

The nucleic acids are purified on a CsCl step gradient consisting of a bottom layer of 5.7M CsCl in TE buffer, and a top layer of 1.0M CsCl in TE. The nucleic acids are incorporated in the top layer. The tubes containing the gradient are centrifuged overnight in a swing-out rotor (e.g. Beckman SW 50.1 at 45,000 rpm). The DNA is collected from the region of the interface, and RNA can be recovered from the bottom of the tube. The DNA is diluted with 2 volumes of water, and precipitated with 2 volumes of ice cold ethanol as in example (a) above. The precipitates are resuspended in TE bufer, precipitated again with ethanol, and used for Southern analysis.

Example 14: Detection of Foreign DNA Sequences in the Genome of Transformed *Dactylis glomerata L.* by Southern Analysis Southern hybridization analysis is performed essentially according to Maniatis et al. ["Molecular Cloning, a Laboratory Manual", Cold Spring Harbor Laboratory (1982)]. *Dactylis glomerata L.* DNA [purified according to examples 13(a) and 13(b)] is cut with restriction enzyme BamHI and 5 µg thereof are loaded per lane, and run on a 1% agarose gel to separate the DNA on the basis of the fragment sizes. The gel is placed in 0.25M HCl for about 20 minutes and then rinsed with $H_2O$, and then placed in 0.4M NaOH for 30 minutes. The DNA is transferred overnight to GeneScreen Plus® (NEN Res. Products, Cat.No. NEF 976, Lot. No. 330GP62) in the normal way (as described in the instruction booklet supplied with the product) using 0.4M NaOH as the transfer buffer. After transfer overnight, the filter is removed, washed with 2×SSC (0.3M NaCl, 0.03M Na citrate) for about 5 minutes, and then air dried. The blot is pre-hybridized for 4 hours at 65° C. with buffer containing 10 g/liter Bovine Serum Albumin (Fat Free Sigma, Cat.No. A-4503), 7% SDS, 1 mM NaEDTA, and 0.52M Sodium Phosphate buffer pH 7.0. A radioactively labelled probe is prepared by the random primer method using the IBI 'Prime Time' labelling kit or any other suitable method, and separating the probe from the nucleotides in a spin column. The probe DNA consists of the fragment of pCIB709 containing the 35S promoter region and the aminoglycoside phosphotransferase type IV structural gene region. Hybridisation is allowed to proceed overnight at 65° C. The blot is then washed in four washes SW wash buffer, the last two washes being carried out at 65° C. The blot is then washed for 2 hours in 0.2×SSC containing 1% SDS and 5 mM NaEDTA at 65° C. The wet blot is wrapped in food film (Saranwrap®) or any other suitable film, and placed in a cassette with Tungsten intensifying screens for exposure with X-ray film (Kodak X-Omat AR film, Eastman Kodak, Rochester, N.Y. 14650, Cat. No. 165 1454). On development, there is clear specific hybridisation of the probe to the DNA coming from callus and plants transformed with pCIB709. The DNA is clearly integrated into the high molecular weight DNA of the transformants.

SW hybridization buffer:

1% (w/v) Bovine Serum Albumin (fat free)

0.52M Sodium phosphate pH 7.0

7% (w/v) SDS 1 mM NaEDTA

Wash solution:

0.04M Sodium phosphate pH 7.0

1 mM NaEDTA

1% (w/v) SDS 0.125M NaCl

Example 15: Cryopreservation of Callus Cultures of *Dactylis glomerata L.*

(1) Actively-growing callus of *Dactylis glomerata L.* is placed into liquid SH-0 medium. 0.5 to 1 g of callus is typically placed into 20 ml of medium. The flask containing the callus is gently shaken and swirled, to disperse and disrupt the clumps of callus. The culture is then cooled on ice. The cryoprotectant solution is also cooled on ice.

(2) An equal volume of cryoprotectant solution P is added over a period of 5 minutes, and the mixture is kept on ice for one hour. During this time, 1.0 ml aliquots are distributed to labeled precooled 1.8 ml plastic cryopreservation vials (Vangard Cryos cryogenic vials, Sumitomo Bakelite Co. Ltd. Japan, Cat.N° MS4502), and kept on ice. Cryoprotectant Solution P consists of 1M Glycerol, 1M L-Proline, 2M Dimethyl Sulfoxide (DMSO, Sigma, Cat. N° D2650, Lot N° 57F-8816) in water, pH 5.6, and is freshly prepared before each use (the glycerol/proline/water mixture may be stored frozen).

(3) After the cells have been exposed to the cryoprotectant solution for a period of about 1 hour, the vials are immersed at the surface of a liquid bath which is at the temperature of 0° C. The bath may consist of ethanol or any other suitable coolant as known in the art. The bath is equipped with a stirring device to keep the coolant mixed, and is connected to an apparatus which can refrigerate the coolant at a controlled rate.

(4) Once the vials are in the coolant, the temperature is reduced at the rate of approximately 0.5° C./minute. When the temperature reaches −40° C., the vials are plunged into liquid nitrogen and then stored in liquid nitrogen, either in the liquid itself or in the vapor above it, at a temperature not to exceed −100° C.

Example 16: Cryopreservation of Embryogenic Suspension Culture Cells of *Dactylis glomerata L.*

(a) (1) A *Dactylis glomerata L.* suspension culture is taken 2 to 10 days after subculture is cooled on ice. The cryoprotectant solution is normally also cooled on ice. The cryoprotectant consists of 1M Glycerol, 1M L-Proline, 2M Dimethyl Sulfoxide (DMSO) in water, pH 5.6. The cryoprotectant solution is freshly prepared before each use or the glycerol/proline/water may be stored frozen.

(2) The cryprotectant is added to the suspension over a period of 5 minutes. The cells are left in the cryoprotectant on ice for one hour. During or after this time, aliquots are distributed to cryopreservation vials and kept on ice. The vials are then treated as described above for callus material in example 15.

(b) Cryopreservation is carried out as described in Example 16(a) except that the cryoprotectant in step (1) consists of 1M Glycerol, 1M Sucrose and 2M DMSO in water at pH 5.6.

Example 17: Recovery of Growing Cultures from Cryopreserved *Dactylis glomerata L.*

(a) (1) A vial prepared as in example 15 is removed from the liquid nitrogen.

(2) The vial is thawed by leaving it at room temperature until all the ice has melted.

(3) The contents of the vial are spread onto SH-0 culture medium solidified with Gelrite® or agar. Typically, 0.5 ml of thawed culture is spread onto each 10 cm diameter petri plate containing 30–50 ml of medium. The solid medium is poured on a slant or a cavity is scooped out of the medium around its periphery in order to aid the drainage of remaining cryoprotectant away from the cells.

(4) The material is incubated on the medium in the dark at 27° C. Growth is readily apparent in 1 to 4 weeks. Callus is then subcultured as for normal embryogenic callus as described above.

(b) Recovery of growing cultures from cryopreserved *Dactylis glomerata L.* is carried out as described in Example 17(a), except that in step (2) the vial is tawed rapidly by agitating it in a water bath at about 40° C. until all the ice has melted.

Example 18: Cryopreservation of *Zea mays* Callus

Cryopreservation of avtively growing *Zea mays* callus is carried out as described for *Dactylis glomerata L.* in Example 15.

Example 19: Cryopreservation of Embryogenic Suspension Culture Cells of *Zea mays*

Cryopreservation of embryogenic suspension culture cells of *Zea mays* is carried out as described for *Dactylis glomerata L.* in Examples 16(a) and 16(b).

Example 20: Recovery of Growing Cultures from Cryopreserved *Zea mays*

Recovery of growing cultures from cryopreserved *Zea mays* is carried out as described for *Dactylis glomerata L.* in Examples 17(a) and 17(b).

LITERATURE

Bright, S. W. J. and Johnes, M. G. K., "Cereal Tissue and Cell Culture" (1985) 204–230, Nijoff, M./Junk, W. Dr., Dordrecht;
Loerz, H., et al., Mol. Gen. Genet., 199 (1985) 178–182;
Potrykus, I., et al., Mo. Gen. Genet., 199 (1985) 183–188;
Fromm, M. E., et al., Nature, 319 (1986) 791–793;
Abdullah, R., et al., Bio/Technology, 4 (1986) 1087–1090;
Yamada, Y., et al., Plant Cell Reports, 5 (1986) 85–88;
Hanning, G. E., et al., Theor. Appl. Genet., 63 (1982) 155–159;
Lu, Ch., et al., Z. Pflanzenphysiol., 104 (1981) 311–318;
Vasil, V., et al., Z. Pflanzenphysiol., 111 (1983) 233–239;
Schenk, R. U. and Hildebrandt, A. C., Can. J. Bot., 50 (1972) 199–204;
Gray, D. J., et al., Plant Cell Tissue Organ Cult., 4 (1985) 123–133;
Kao, K. N., et al., Planta, 126 (1975) 105–110;
Potrykus, I., et al., Theor. Appl. Genet., 54 (1979) 209–214;
Maniatis et al., "Molecular Cloning, a Laboratory Manual", Cold Spring Habor Laboratory (1982);
Shillito, R. D., et al., Plant cell Reports, 2 (1983) 244–247;
Shillito, R. D., et al., European Patent Application EP-0, 129,688;
Adams, T. L., et al., Plant Cell Reports, 2 (1983) 165–168;
Heide, Physiol. Plantarum, 70 (1987) 523–529;
Murashige, T., et al., Physiol. Plant., (1962) 473–497;
Paszkowski, J., et al., The EMBO Journal, 3 (1984) 2717–2722;
Paszkowski, J., et al., European Patent Application EP-0, 164,575;
Shillito, R. D., et al., Bio/Technology, 3 (1985) 1099–1103;
Mettler, I. J., British Patent Application GB-2,140,822;
Negrutiu, I., et al., Plant Mol. Biology, 8 (1987) 363–373;
Ryan, C., et al., Ann. Rev. Plant Physiol., 24 (1973) 173–196;
Lipke, H., et al., J. Agr. Food Chem., 2 (1954) 410–414;
Birk, Y., et al., Biochim. Biophys. Acta, 67 (1963) 326–328;
Hilder, V. A., et al., Nature, 330 (1987) 160–163;
Hammond et al., J. Biol. Chem., 259 (1984) 9883–9890;
Wienand, U., et al., Mol. Gen. Genet., 182 (1981) 440–444;
Pennica, P., et al., Nature, 301 (1983) 214;
Stephien, P., et al., Gene, 24 (1983) 281–297;
Itakura, K., et al., J. Am. Chem. Soc., 97 (1975) 7327;
Odell, J. T., et al., Nature, 313 (1985) 810;
Rhodes, C., et al., Biotechnology, 52 (1988) 56–60;
Gainborg, O. et al., Exp. Cell Res., 50 (1968) 151–158;
Skene, K. G. M., et al., Zeitschr.Pflanzenzuechtung, 90 (1983) 130–135;
Ahloowalia, B. S., Crop Science, 15 (1975) 449–452;
Kasperbauer, M. J., et al., Crop Science, 19 (1979) 457–460;
Lo, P. F., et al., Crop Science, 20 (1980) 363–367;
Krans, J. V., et al., Crop Science 22 (1982) 1193–1197;
Randolph, L. F., J. Agric. Research, 53 (1936) 881–916;
Brown, W. V., Phytomorphology, 10 (1960) 215–223;
Barton, K. A., et al., Plant Physiol., 85 (1987) 1103–1109;
Vaeck, M., et al., Nature, 328 (1987) 33–37;
Cocking, E. C., and Davey, M. R., Science, 236 (1987) 1259–1262;
Ahloowalia, B. S., Handbook of Plant Cell Culture, Ammirato, et al. (eds) Macmillan, N.Y., (1984) 91–125;
George, E. F., et al. (eds), Exegetics Ldt., Edington, Westbury, Wiltshire, England (1987);
Luehrs, R., and Loerz, H., Theor. Appl. Genet., 75 (1987) 16–25;
Withers, L. A., Plant Tissue Culture and its Agricultural Application; Withers, L. A., and Alderson, P. G. (eds), University Press, Cambridge, England (1986) 261–276;
Abel, P. P., et al., Science, 233 (1986) 738;
Roger and Bendich, Plant Mol. Biology, 5 (1985) 69–76;
Gritz, L., and Davis, J., Gene, 25 (1983) 179–188;
Rothstein, S., et al., Gene, 53 (1987) 153–161.

SEQUENCE 1: NUCLEOTIDE SEQUENCE OF THE PLASMID PCIB709.

```
   1  TCGCGCGTTT CGGTGATGAC GGTGAAAACC TCTGACACAT GCAGCTCCCG
  51  GAGACGGTCA CAGCTTGTCT GTAAGCGGAT GCCGGGAGCA GACAAGCCCG
 101  TCAGGGCGCG TCAGCGGGTG TTGGCGGGTG TCGGGGCTGG CTTAACTATG
 151  CGGCATCAGA GCAGATTGTA CTGAGAGTGC ACCATATGCG GTGTGAAATA
 201  CCGCACAGAT GCGTAAGGAG AAAATACCGC ATCAGGCGCC ATTCGCCATT
 251  CAGGCTGCGC AACTGTTGGG AAGGGCGATC GGTGCGGGCC TCTTCGCTAT
 301  TACGCCAGCT GGCGAAAGGG GGATGTGCTG CAAGGCGATT AAGTTGGGTA
 351  ACGCCAGGGT TTTCCCAGTC ACGACGTTGT AAAACGACGG CCAGTGAATT
 401  CGAGCTCGGT ACCCGGAGAT CTGGATTTTA GTACTGGATT TTGGTTTTAG
 451  GAATTAGAAA TTTTATTGAT AGAAGTATTT TACAAATACA AATACATACT
 501  AAGGGTTTCT TATATGCTCA ACACATGAGC GAAACCCTAT AAGAACCCTA
 551  ATTTCCCTTA TCGGGAAACT ACTCACACAT TAGGATCCCG GTCGGCATCT
 601  ACTCTATTCC TTTGCCCTCG GACGAGTGCT GGGGCGTCGG TTTCCACTAT
 651  CGGCGAGTAC TTCTACACAG CCATCGGTCC AGACGGCCGC GCTTCTGCGG
 701  GCGATTTGTG TACGCCCGAC AGTCCCGGCT CCGGATCGGA CGATTGCGTC
 751  GCATCGACCC TGCGCCCAAG CTGCATCATC GAAATTGCCG TCAACCAAGC
 801  TCTGATAGAG TTGGTCAAGA CCAATGCGGA GCATATACGC CCGGAGCCGC
 851  GGCGATCCTG CAAGCTCCGG ATGCCTCCGC TCGAAGTAGC GCGTCTGCTG
 901  CTCCATACAA GCCAACCACG GCCTCCAGAA GAAGATGTTG GCGACCTCGT
 951  ATTGGGAATC CCCGAACATC GCCTCGCTCC AGTCAATGAC CGCTGTTATG
1001  CGGCCATTGT CCGTCAGGAC ATTGTTGGAG CCGAAATCCG CGTGCACGAG
1051  GTGCCGGACT TCGGGGCAGT CCTCGGCCCA AAGCATCAGC TCATCGAGAG
1101  CCTGCGCGAC GGACGCACTG ACGGTGTCGT CCATCACAGT TGCCAGTGA
1151  TACACATGGG GATCAGCAAT CGCGCATATG AAATCACGCC ATGTAGTGTA
1201  TTGACCGATT CCTTGCGGTC CGAATGGGCC GAACCCGCTC GTCTGGCTAA
1251  GATCGGCCGC AGCGATCGCA TCCATGGCCT CCGCGACCGG CTGCAGAACA
1301  GCGGGCAGTT CGGTTTCAGG CAGGTCTTGC AACGTGACAC CCTGTGCACG
1351  GCGGGAGATG CAATAGGTCA GGCTCTCGCT GAATTCCCCA ATGTCAAGCA
```

SEQUENCE 1: NUCLEOTIDE SEQUENCE OF THE PLASMID PCIB709.

```
1401 CTTCCGGAAT CGGGAGCGCG GCCGATGCAA AGTGCCGATA AACATAACGA
1451 TCTTTGTAGA AACCATCGGC GCAGCTATTT ACCCGCAGGA CATATCCACG
1501 CCCTCCTACA TCGAAGCTGA AAGCACGAGA TTCTTCGCCC TCCGAGAGCT
1551 GCATCAGGTC GGAGACGCTG TCGAACTTTT CGATCAGAAA CTTCTCGACA
1601 GACGTCGCGG TGAGTTCAGG CTTTTTCATA TCTCATTGCC CCCCGGGATC
1651 CTTATAGAGA GAGATAGATT TGTAGAGAGA GACTGGTGAT TTCAGCGTGT
1701 CCTCTCCAAA TGAAATGAAC TTCCTTATAT AGAGGAAGGG TCTTGCGAAG
1751 GATAGTGGGA TTGTGCGTCA TCCCTTACGT CAGTGGAGAT ATCACATCAA
1801 TCCACTTGCT TTGAAGACGT GGTTGGAACG TCTTCTTTTT CCACGATGCT
1851 CCTCGTGGGT GGGGGTCCAT CTTTGGGACC ACTGTCGGCA GAGGCATCTT
1901 GAACGATAGC CTTTCCTTTA TCGCAATGAT GGCATTTGTA GGTGCCACCT
1951 TCCTTTTCTA CTGTCTTCAT GATGAAGTGA CAGATAGCTG GGCAATGGAA
2001 TCCGAGGAGG TTTCCGGAAA TTACCCTTTG TTGAAAAGTC TCAATTGCCC
2051 TTTGGTCTTC TGAGACTGTA TCCTTGATAT TTTTGGAGTA GACCAGAGTG
2101 TCGTGCTCCA CCATGTTGAC GAAGATTTTC TTCTTGTCAT TGAGTCGTAA
2151 GAGACTCTGT ATGAACTGTT CGCCAGTTTT CACGGCGAGT TCTGTTAGAT
2201 CCTCGATTTG AATCTTTGAC TCCATGGCCT TTGATTCAGT AGGAACTACT
2251 TTTTTAGAGA CTCCAATCTC TATTACTTGC CTTGGTTTAT GAAGCAAGCC
2301 TTGAATCGTC CATACTGGAA TAGTACTTCT GATCTTGGAG AAATATATCT
2351 TTCTCTGTGT TCTTGATGCA GTTAGTCCTG AATCTTTTGA CTGCATCTTT
2401 AACCTTCTTG GGAAGGTATT TGATCTCCTG GAGATTATTA CTCGGGTAGA
2451 TCGTCTTAAT GAGACCTGCT GCGTAGGCCT CTCTAACCAT CTGTGGGTTA
2501 GCGTTCTTTC TGAAATTGAA GAGGCTAATC TTCTCATTAT CAGTGGTGAA
2551 CATAGTATCG TCACCTTCAC CGTCGAACTT TCTTCCTAGA TCGTAGAGAT
2601 AGAGGAAGTC GTCCATTGTA ATCTCCGGGG CAAAGGAGAT CCTCTAGAGT
2651 CGACCTGCAG GCATGCAAGC TTGGCGTAAT CATGGTCATA GCTGTTTCCT
2701 GTGTGAAATT GTTATCCGCT CACAATTCCA CACAACATAC GAGCCGGAAG
2751 CATAAAGTGT AAAGCCTGGG GTGCCTAATG AGTGAGCTAA CTCACATTAA
2801 TTGCGTTGCG CTCACTGCCC GCTTTCCAGT CGGGAAACCT GTCGTGCCAG
2851 CTGCATTAAT GAATCGGCCA ACGCGCGGGG AGAGGCGGTT GCGTATTGG
2901 GCGCTCTTCC CGTTCCTCGC TCACTGACTC GCTGCGCTCG GTCGTTCGGC
2951 TGCGGCGAGC GGTATCAGCT CACTCAAAGG CGGTAATACG GTTATCCACA
3001 GAATCAGGGG ATAACGCAGG AAAGAAGATG TGATCAAAAG GCCAGCAAAA
3051 GGCCAGGAAC CGTAAAAAGG CCGCGTTGCT GGCGTTTTTC CATAGGCTCC
3101 GCCCCCCTGA CGAGCATCAC AAAAATCGAC GCTCAAGTCA GAGGTGGCGA
3151 AACCCGACAG GACTATAAAG ATACCAGGCG TTTCCCCCTG GAAGCTCCCT
3201 CGTGCGCTCT CCTGTTCCGA CCCTGCCGCT TACCGGATAC CTGTCCGCCT
3251 TTCTCCCTTC GGGAAGCGTG GCGCTTTCTC AATGCTCACG CTGTAGGTAT
3301 CTCAGTTCGG TGTAGGTCGT TCGCTCCAAG CTGGGCTGTG TGCACGAACC
3351 CCCCGTTCAG CCCGACCGCT GCGCCTTATC CGGTAACTAT CGTCTTGAGT
3401 CCAACCCGGT AAGACACGAC TTATCGCCAC TGGCAGCAGC CACTGGTAAC
3451 AGGATTAGCA GAGCGAGGTA TGTAGGCGGT GTCACAGAGT TCTTGAAGTG
3501 GTGGCCTAAC TACGGCTACA CTAGAAGGAC AGTATTTGGT ATCTGCGCTC
3551 TGCTGAAGCC AGTTACCTTC GAAAAAAGAG TTGGTAGCTC TTGATCCGGC
3601 AAACAAACCA CCGCTGGTAG CGGTGGTTTT TTTGTTTGCA AGCAGCAGAT
3651 TACGCGCAGA AAAAAAGGAT CTCAAGAAGA TCCTTTGATC TTTTCTACGG
3701 GGTCTGACGC TCAGTGGAAC GAAAACTCAC GTTAAGGGAT TTTGGTCATG
3751 AGATTATCAA AAAGGATCTT CACCTAGATC CTTTTAAATT AAAAATGAAG
3801 TTTTAAATCA ATCTAAAGTA TATATGAGTA AACTTGGTCT GACAGTTACC
3851 AATGCTTAAT CAGTGAGGCA CCTATCTCAG CGATCTGTCT ATTTCGTTCA
3901 TCCATAGTTG CCTGACTCCC CGTCGTGTAG ATAACTACGA TACGGGAGGG
3951 CTTACCATCT GGCCCCAGTG CTGCAATGAT ACCGCGAGAC CCACGCTCAC
4001 CGGCTCCAGA TTTATCAGCA ATAAACCAGC CAGCCGGAAG GGCCGAGCGC
4051 AGAAGTGGTC CTGCAACTTT ATCCGCCTCC ATCCAGTCTA TTAATTGTTG
4101 CCGGGAAGCT AGAGTAAGTA GTTCGCCAGT TAATAGTTTG CGCAACGTTG
4151 TGGCCATTGC TACAGGCATC GTGGTGTCAC GCTCGTCGTT TGGTATGGCT
4201 TCATTCAGCT CCGGTTCCCA AGCATCAAGG CGAGTTACAT GATCCCCCAT
4251 GTTGTGCAAA AAAGCGGTTA GCTCCTTCGG TCCTCCGATC GTTGTCAGAA
4301 GTAAGTTGGC CGCAGTGTTA TCACTCATGG TTATGGCAGC ACTGCATAAT
4351 TCTCTTACTG TCATGCCATC CGTAAGATGC TTTTCTGTGA CTGGTGAGTA
4401 CTCAACCAAG TCATTCTGAG AATAGTGTAC GTGGCGACCG AGTTGCTCTT
4451 GCCCGGCGTC AATACGGGAT AATACCGCGC CACATAGCAG AACTTTAAAA
4501 GTGCTCATCA TTGGAAAACG TTCTTCGGGG CGAAAACTCT CAAGGATCTT
4551 ACCGCTGTTG AGATCCAGTT CGATGTAACC CACTCGTGCA CCCAACTGAT
4601 CTTCAGCATC TTTTACTTTC ACCAGCGTTT CTGGGTGAGC AAAAACAGGA
4651 AGGCAAAATG CCGCAAAAAA GGGAATAAGG GCGACACGGA AATGTTGAAT
4701 ACTCATACTC TTCCTTTTTC AATATTATTG AAGCATTTAT CAGGGTTATT
4751 GTCTCATGAG CGGATACATA TTTGAATGTA TTTAGAAAAA TAAACAAATA
4801 GGGGTTCCGC GCACATTTCC CCGAAAAGTG CCACCTGACG TCTAAGAAAC
4851 CATTATTATC ATGACATTAA CCTATAAAAA TAGGCGTATC AGCAGGCCCT
4901 TTCGTC
```

What is claimed is:

1. A method of producing protoplasts of graminaceous plants selected from the group consisting of *Dactylis glomerata* and wheat, which protoplasts comprise stably incorporated exogenous DNA and are capable of being regenerated into plants, which method comprises:

a) isolating tissue from the basal portion of young inner leaves of *Dactylis glomerata* or wheat plants;

b) culturing the tissue in a medium capable of inducing the formation of embryogenic callus and embryos;

c) initiating embryogenic suspension cultures in a suitable liquid medium comprising dicamba;

d) periodically transferring supernatant medium containing small cell clusters to fresh medium;

e) repeating step d) until an embryogenic suspension culture is obtained which culture is essentially free of non-embryogenic cells and the majority of embryogenic cell clusters are about 150 to about 2000 um in size;

f) removing cell walls with suitable enzymes and isolating the resulting protoplasts; and g) treating the protoplasts with exogenous DNA to form protoplasts comprising stably incorporated exogenous DNA.

2. A method of producing graminaceous plants selected from the group consisting of *Dactylis glomerata* and wheat, which plants comprise plant cells derived from protoplasts, which plant cells comprise stably incorporated exogenous DNA, which method comprises:

a) isolating tissue from the basal portion of young inner leaves of *Dactylis glomerata* or wheat plants;

b) culturing the tissue in a medium capable of inducing the formation of embryogenic callus and embryos;

c) initiating embryogenic suspension cultures in a suitable liquid medium comprising dicamba;

d) periodically transferring supernatant medium containing small cell clusters to fresh medium;

e) repeating step d) until an embryogenic suspension culture is obtained which culture is essentially free of non-embryogenic cells and the majority of embryogenic cell dusters are about 150 to about 2000 um in size;

f) removing the cell walls with suitable enzymes and isolating protoplasts;

g) treating the protoplasts with exogenous DNA to form transformed protoplasts comprising stably incorporated exogenous DNA;

h) forming embryogenic callus and embryos from the transformed protoplasts by first culturing said transforms protoplasts in a solid medium comprising about 30–40% conditioned media and O-acetyl salicylic acid or a derivative of O-acetyl salicylic acid, and subsequently transferring said transformed protoplasts to liquid media using the bead culture technique; and i) regenerating plants from the transformed protoplasts.

3. A *Dactylis glomerata* protoplast capable of being regenerated into plants.

4. A protoplast according to claim 3 wherein said regenerated plants are fertile plants.

5. A protoplast according to claim 3 wherein said protoplast comprises stably incorporated exogenous DNA.

6. A method of producing protoplasts of graminaceous plants of *Dactylis glomerata*, which protoplasts are capable of being regenerated into plants, which method comprises:

a) isolating tissue from the basal portion of young inner leaves of *Dactylis glomerata* plants;

b) culturing the tissue in a medium capable of inducing the formation of embryogenic callus and embryos;

c) initiating embryogenic suspension cultures in a suitable liquid medium comprising dicamba;

d) periodically transferring supernatant medium containing small cell clusters to fresh medium;

e) repeating step d) until an embryogenic suspension culture is obtained which culture is essentially free of non-embryogenic cells and the majority of embryogenic cell clusters are about 150 to about 2000 um in size;

f) removing cell walls with suitable enzymes and isolating the resulting protoplasts.

7. A method of producing graminaceous plants of *Dactylis glomerata*, which plants comprise plant cells derived from protoplasts, which plant cells comprise stably incorporated exogenous DNA, which method comprises:

a) isolating tissue from the basal portion of young inner leaves of *Dactylis glomerata* plants, b) culturing the tissue in a medium capable of inducing the formation of embryogenic callus and embryos;

c) initiating embryogenic suspension cultures in a suitable liquid medium comprising dicamba;

d) periodically transferring supernatant medium containing small cell clusters to fresh medium;

e) repeating step d) until an embryogenic suspension culture is obtained which culture is essentially flee of non-embryogenic cells and the majority of embryogenic cell clusters are about 150 to about 2000 um in size;

f) removing the cell walls with suitable enzymes and isolating protoplasts;

g) treating the protoplasts with exogenous DNA to form transformed protoplasts comprising stably incorporated exogenous DNA;

h) forming embryogenic callus and embryos from the transformed protoplasts by first culturing said transformed protoplasts in a solid medium comprising about 30–40% conditioned media and O-acetyl salicylic acid or a derivative of O-acetyl salicylic acid, and subsequently transferring said transformed protoplasts to liquid media using the bead culture technique; and i) regenerating plants from the transformed protoplasts.

8. A transformed graminaceous plant of *Dactylis glomerata* comprising stably incorporated exogenous DNA, said plant being obtained using the method of claim 7, wherein said exogenous DNA confers upon said graminaceous plants a phenotype selected from the group consisting of resistance to a bacteria, resistance to a fungus, resistance to a virus, resistance to an insect, resistance to a herbicide, resistance to a cytotoxin, resistance to adverse environmental influences and expression of mammalian specific protein.

9. Graminaceous plants selected from the group consisting of *Dactylis glomerata* and wheat and propagules thereof comprising plant cells containing stably incorporated exogenous DNA, wherein said exogenous DNA does not naturally occur in said graminaceous plants.

10. Graminaceous plants according to claim 9, wherein said exogenous DNA comprises a chimeric gene.

11. Graminaceous plants according to claim 10, wherein said chimeric gene is capable of expressing a protein in said plants.

12. Graminaceous plants according to claim 11, wherein said protein does not naturally occur in said plants.

13. Graminaceous plants according to claim 12, wherein said protein is a Bacillus insect toxin.

* * * * *